United States Patent [19]

Christensen et al.

[11] 4,309,346
[45] Jan. 5, 1982

[54] PROCESS FOR THE PREPARATION OF 1-CARBAPENEMS AND INTERMEDIATES VIA TRITHIOORTHOACETATES

[75] Inventors: Burton G. Christensen, Scotch Plains; Ronald W. Ratcliffe, Matawan; Thomas N. Salzmann, North Plainfield, all of N.J.

[73] Assignee: Merck & Co., Inc., Rahway, N.J.

[21] Appl. No.: 134,396

[22] Filed: Mar. 27, 1980

[51] Int. Cl.³ .................. C07D 205/08; C07D 487/04
[52] U.S. Cl. .......................... 260/239 A; 260/245.2 T
[58] Field of Search .................................. 260/239 A

[56] References Cited

U.S. PATENT DOCUMENTS 4,122,262  10/1978  Buckley et al. .................. 260/239 A

*Primary Examiner*—Mark L. Berch
*Attorney, Agent, or Firm*—James A. Arno; Hesna J. Pfeiffer

[57] ABSTRACT

Disclosed is a process for the total synthesis of 1-carbapenem antibiotics (I) from L-aspartic acid via intermediates II and III:

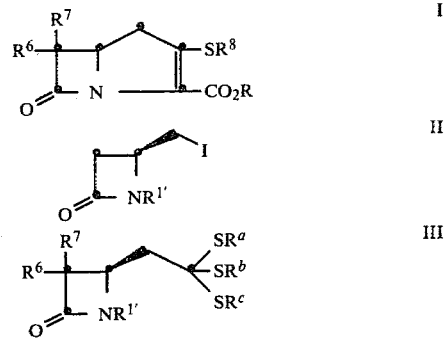

wherein R is hydrogen, a pharmaceutically acceptable ester moiety or salt cation, or a readily removable blocking group; $R^6$ and $R^7$ are, inter alia, independently selected from the group consisting of hydrogen, alkyl, alkenyl, aryl and aralkyl; $R^{1'}$ is hydrogen or a protecting group; and $R^a$, $R^b$ and $R^c$ are independently selected from alkyl, aryl and aralkyl.

8 Claims, No Drawings

PROCESS FOR THE PREPARATION OF 1-CARBAPENEMS AND INTERMEDIATES VIA TRITHIOORTHOACETATES

BACKGROUND OF THE INVENTION

This invention relates to the total synthesis of certain 1-carbapenems and their pharmaceutically acceptable salt, ester and amide derivatives which are useful as antibiotics. Such compounds may generically be represented by the following structural formula (I):

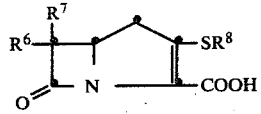

wherein $R^6$, $R^7$, and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl; wherein the substituent or substituents relative to the above-named radicals are selected from the group consisting of:

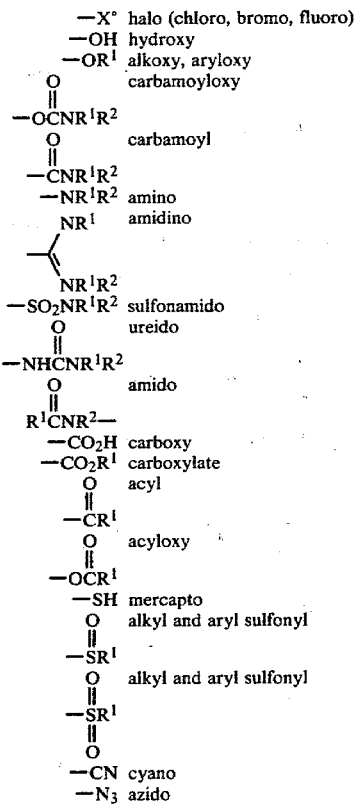

wherein, relative to the above listed substituents on $R^6$, $R^7$, and $R^8$, the groups $R^1$ and $R^2$ are independently selected from: hydrogen, alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl and wherein the hetero atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms.

This invention also relates to the carboxyl derivatives of I which are antibiotics and which may be represented by the following generic structure (I):

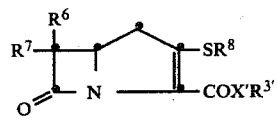

wherein X' is oxygen, sulphur or NR' (R'=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in greater detail below.

Starting from L-aspartic acid, the process proceeds via intermediates II, III, IV and V:

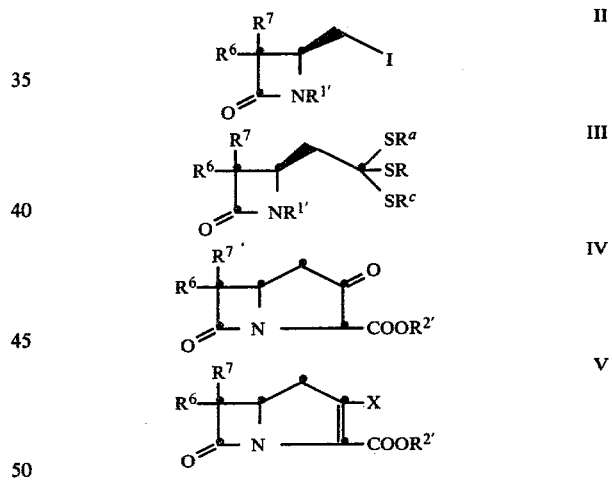

wherein: $R^6$ and $R^7$ are previously defined; X is a conventional leaving group and $R^{2'}$ is hydrogen, a pharmaceutically acceptable ester moiety or a conventional, readily removable protecting group or salt cation. For intermediates IV, $R^{2'}$ is as defined but preferably is an ester moiety defined under $R^{2'}$. $R^{1'}$ is hydrogen or a readily removable protecting group such as a triorganosilyl group. $R^a$, $R^b$ and $R^c$ are independently selected from alkyl, aryl and aralkyl. The details of the total synthesis are given below.

The final compounds prepared by the process of this invention are disclosed and claimed in the following co-pending, commonly assigned U.S. patent application Ser. No. 843,375 abandoned filed Oct. 19, 1977; U.S. patent application Ser. No. 933,681 abandoned filed Aug. 17, 1978; U.S. patent application Ser. No. 31,694 filed Apr. 19, 1979 and in concurrently filed U.S. patent application Ser. Nos. 134,604 filed Mar. 27, 1980; 129,851, filed Mar. 27, 1980 abandoned; 134,381, filed Mar. 27, 1980 and now abandoned. To the extent that the foregoing U.S. Patent Applications describe the antibiotic utility of final compounds I and to the extent that they define substituents $R^6$, $R^7$, $R^8$, $R'$, $X'$ and $R^{3'}$ they are hereby incorporated by reference.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The process of the present invention may conveniently by summarized by the following reaction diagram:

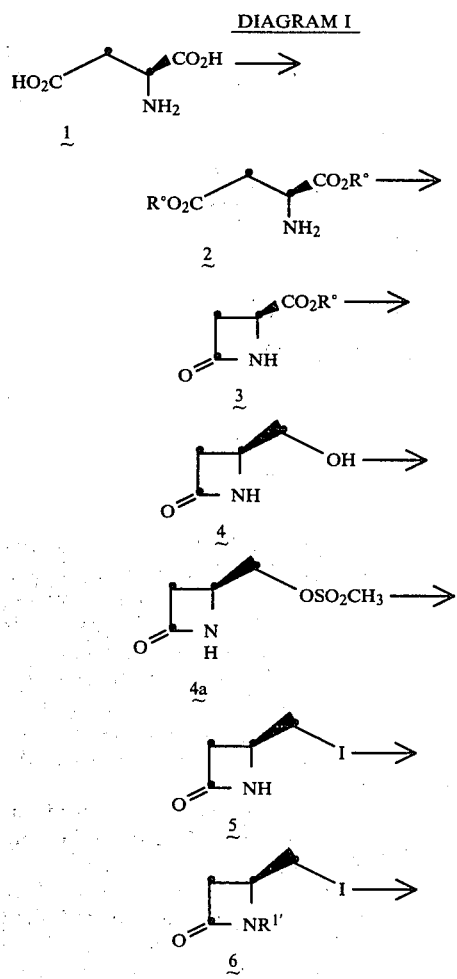

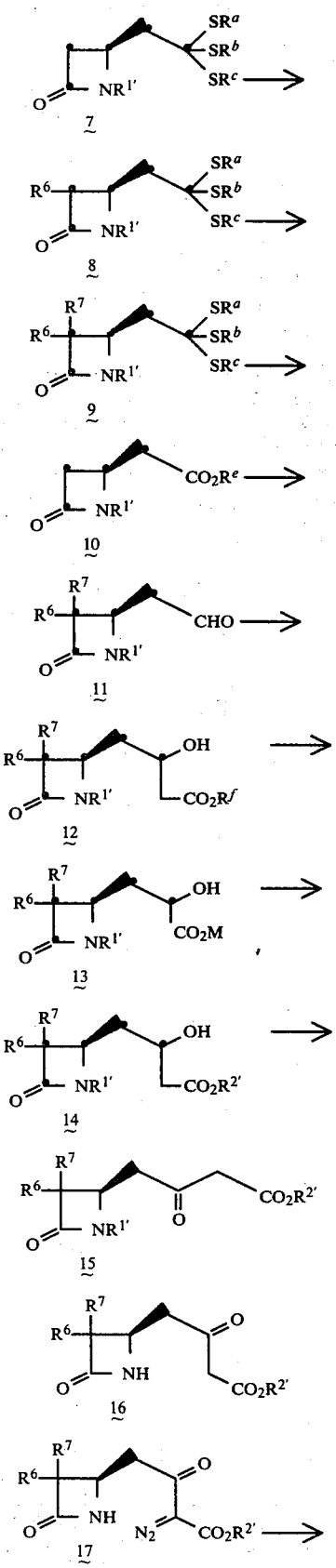

-continued
DIAGRAM 1

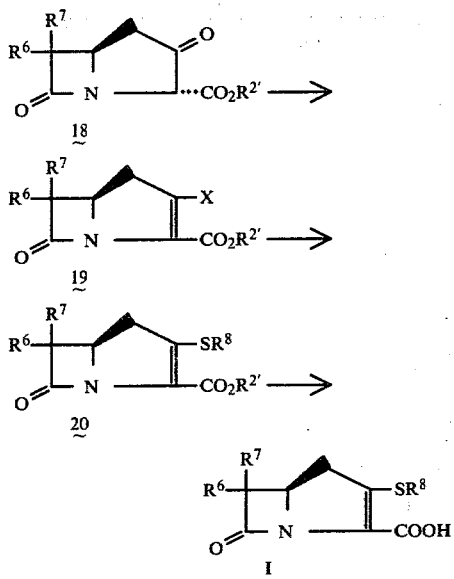

In words relative to the above diagram, L-aspartic acid 1 is esterified according to well known procedures. R° is a protecting group such as benzyl, methyl, ethyl, isopropyl or the like. Typically 1 in a solvent such as benzene, toluene, chloroform or the like is treated with an esterifying agent such as benzyl alcohol, methanol, ethanol, isopropanol, or the like in the presence of p-toluene sulfonic acid HCl, HBr, or the like at a temperature of from 0° to 110° C. for from 1 to 24 hours to achieve the desired establishment and hence protection of the carboxyl functions. The resulting species 2 in a solvent such as ether, THF, DME or the like is treated with trimethylchlorosilane, or the like followed by treatment with EtMgBr, MeMgI, φMgBr, t-BuMgCl, or the like at a temperature of from −40° to 50° C. for from 1 to 72 hours to provide azetidinone 3. Reduction of species 3 with a reducing agent such as NaBH$_4$, or the like in a solvent such as methanol, ethanol, isopropanol or the like at a temperature of from −10° to 40° C. for from 1 to 6 hours provides 4. (For purposes here, the symbols: Et, Me, φ, iPr, and t-Bu stand for: ethyl, methyl, phenyl, isopropyl, and tert-butyl, respectively.)

Treatment of 4 in a solvent such as methylene chloride, CHCl$_3$ or the like with methane sulfonyl chloride, methane sulfonic anhydride or the like in the presence of a base such as Et$_3$N, iPr$_2$NEt, or the like followed by treatment with a stoichiometric to 5 fold excess of sodium iodide in acetone yields 5 via 4a.

The transformation 5→6 establishes the protecting group R$^1$' which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R$^1$' is established by treating 5 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° to 25° C. for from 0.5 to 24 hours in the presence of a base such as triethylamine, diisopropylethylamine, or imidazole.

The transformation 6→7 is accomplished by treating 6 in a solvent such as tetrahydrofuran, dimethoxyethane, diethylether or the like with a carbanion generically represented by the following structure:

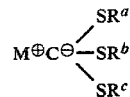

wherein M is a metal cation such as lithium, potassium, copper or magnesium, for example, and R$^a$, R$^b$ and R$^c$ are selected from alkyl, aryl or aralkyl such as methyl, ethyl, benzyl, methoxybenzyl, trityl and phenyl, for example, at a temperature of from −100° to 0° C. and from 0.5 to 4 hours.

Typically, the carbanion reagent is prepared prior to addition of substrate 6 on treatment of the triorganothiomethane with a strong base such as n-butyllithium, t-butyllithium, phenyllithium, lithium diisopropylamide(LDA) or the like.

Resulting intermediate 7 can be mono-, or dialkylated at ring position 3. Alkylation of 7 provides 8. Typically, 7 is treated with a strong base such as lithium diisopropylamide, lithium 2,2,6,6-tetramethylpiperidide, potassium hydride, lithium hexamethyldisilazide, phenyllithium or the like in a solvent such as tetrahydrofuran(THF), hexamethylphosphoramide, ether, dimethoxyethane, and the like at a temperature or from −80° C. to 0° C. whereupon the alkylating agent of choice, R$^6$X° is added (X° is chloro, iodo or bromo); alternatively the alkylating agent may be R$^6$-tosylate, R$^6$-mesylate or an aldehyde or ketone such as acetaldehyde to provide monoalkylated species 8. When desired, dialkylated species 9 may be obtained from 8 by repeating the alkylating procedures 7→8.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing R$^6$ and R$^7$.

The following list is representative of useful alkylating agents for establishing R$^6$ and R$^7$, according to the above scheme: 7→8→9 (this will be referred to as Scheme I, to be distinguished from Scheme II, below, which involves acylation):

| Alkylating Agents | |
|---|---|
| CH$_3$CHO | |
| φCH$_2$CHO | φ = phenyl |
| φCH$_2$CH$_2$CHO | |
| CH$_2$O | |
| CH$_3$I | |
| φCH$_2$Br | |
| CH$_3$COCH$_3$ | |
| CH$_2$=CHCH$_2$Br | |
| CH$_3$C(CH$_3$)=CHCH$_2$Br | |
| CH$_3$OCH$_2$CHO | |
| CH$_3$CH$_2$I | |
| (CH$_3$)$_2$CHI | |
| N$_3$CH$_2$CHO | |
| Me$_2$NCH$_2$CHO | |
| RO$_2$CCH$_2$Br | R = CH$_3$, benzyl, p-nitrobenzyl |
| CF$_3$CF$_2$CHO | |
| RO$_2$CCH$_2$CHO | R = CH$_3$, benzyl, p-nitrobenzyl |
| CH$_3$CH(CH$_3$)CHO, | |

-continued

| Alkylating Agents |
|---|
| CH₃(CH₃)CHCH₂CHO, |
| CH₃CH₂CHO, |
| CH₂=CH—CHO |
| 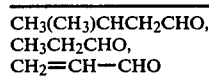 |
| CF₃CHO, |
|  |
| 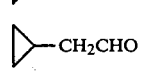 |
|  |
| 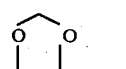 |
| 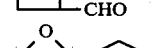 |
| 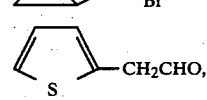 |
| [(CH₃)₃C][(CH₃)₂SiOCH₂C(O)H |
| F₂CHC(O)H |
| FCH₂C(O)H |
|  |
| 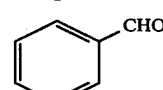 |
| 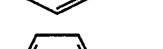    R = protecting group |
| 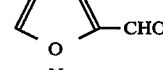 |
| 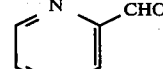 |
| 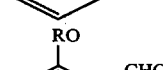 |
| 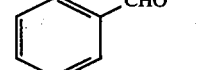 |
| 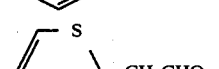 |
| 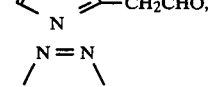 |
| 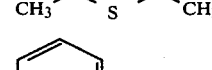 |

-continued

| Alkylating Agents |
|---|
| 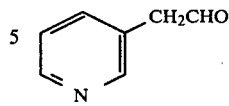 |
| 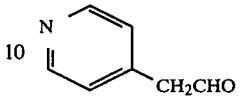 |
| 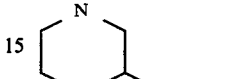 |
| 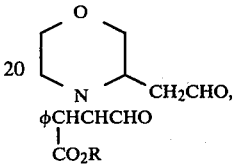 |
| φCHCHCHO<br>\|<br>CO₂R |

R is removable carboxyl protecting group, such as benzyl.

As mentioned above, the 6-substituents may also be established by acylation. Utilization of such acylating agents may be demonstrated in the following manner with regard to a preferred starting, or intermediate, material 8, 9:

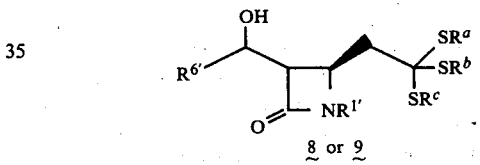

8 or 9 wherein $R^7$ and $R^{1'}$ are as defined above. $R^{6'}$ is defined relative to the definition of $R^6$ and in that sense is the balance of the previously identified group $R^6$. In other words, for purposes of this definition $R^{6'}CH(OH-)=R^6$. An especially preferred material 9 is when $R^7$ is hydrogen and $R^{6'}$ is methyl. Such preferred starting materials are described in the following co-pending, commonly assigned U.S. patent application Ser. No. 34,052 filed Apr. 27, 1979 which is incorporated herein by reference. Basically, such 1'-hydroxy $R^{6'}$ species (8, 9) are prepared according to the following scheme:

SCHEME II

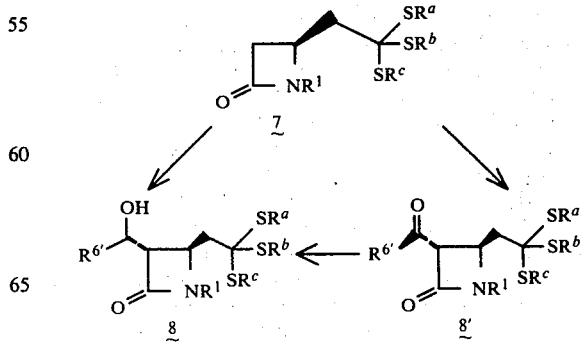

The alkylation $\underset{\sim}{7} \rightarrow \underset{\sim}{8}$, is accomplished as previously described, by treating $\underset{\sim}{7}$ in a solvent such as tetrahydrofuran, dimethoxyethane, diethylether, hexamethylphosphoramide, at a temperature of from $-100°$ to $-20°$ C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form $\underset{\sim}{8}$ or $\underset{\sim}{9}$ can be conveniently separated by chromatography or crystallization.

Intermediate $\underset{\sim}{7}$ may proceed directly to $\underset{\sim}{8}$ as indicated above, Scheme I, or it may take the circuitous path via $\underset{\sim}{8'}$. The direct acylation, to $\underset{\sim}{8'}$ is accomplished by treating $\underset{\sim}{7}$ with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from $-100°$ to $-20°$ C. with an acylating agent such as N-acyl imidazole or the like. Addition of the $\underset{\sim}{7}$ plus base mixture to the acylating agent is preferred.

Representative acylating agents for this scheme $\underset{\sim}{7} \rightarrow \underset{\sim}{8'} \rightarrow \underset{\sim}{8}$ are listed below.

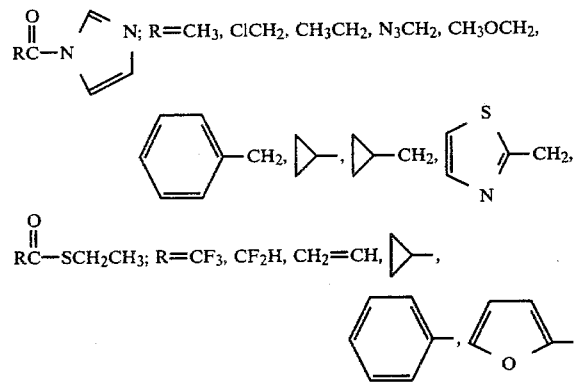

Further with respect to Scheme II, the reduction $\underset{\sim}{8'} \rightarrow \underset{\sim}{8}$ is accomplished by contacting the ketone with a reducing agent such as potassium tri(sec-butyl)borohydride, lithium tris(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from $-78°$ to $25°$ C. The reaction can conveniently be conducted in the presence of an added complexing salt such as potassium iodide, magnesium bromide or the like.

In a similar manner, unresolved $\underset{\sim}{8}$ (cis and trans) may be oxidized to $\underset{\sim}{8'}$ for reduction to $\underset{\sim}{8}$ as indicated above:

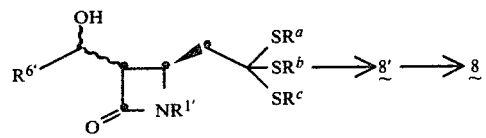

The oxidation is accomplished with an oxidizing agent such as dipyridine chromium (VI) oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from $-78°$ to $25°$ C. for from 5 minutes to 5 hours.

Now return to the main scheme of synthesis, Diagram I, and the transformation $\underset{\sim}{9} \rightarrow \underset{\sim}{10}$, which is accomplished by treating $\underset{\sim}{9}$ in a solvent such as methanol, ethanol, isopropanol, water or the like at a temperature of from 0° to 80° C. with a Lewis acid such as mercuric chloride, silver tetrafluoroborate, thallium trinitrate or the like. The value of $R^e$ is determined by the identity of the alcohol taken in reaction.

If, relative to $\underset{\sim}{10}$, $R^6$ or $R^7$ bear any functional groups, such as OH, which might interfere with subsequent steps, it is convenient to cover them at this stage. For example, if the offending group is OH, a preferred protecting group is triorganosilyl, such as t-butyldimethylsilyl, t-butyldiphenylsilyl, triphenylsilyl, and the like. Typically, silylation is accomplished by treating $\underset{\sim}{10}$ with the corresponding triorganosilyl chloride in a solvent such as dimethylformamide, acetonitrile, tetrahydrofuran and the like at a temperature of from $-20°$ to $80°$ C. for from 0.5 to 24 hours.

The reduction $\underset{\sim}{10} \rightarrow \underset{\sim}{11}$ is accomplished by treating $\underset{\sim}{10}$ in a solvent such as toluene, methylene chloride diethylether, tetrahydrofuran and the like with a reducing agent such as diisobutylaluminum hydride, sodium bis(2-methoxyethoxy)aluminum hydride or the like at a temperature of from $-100°$ to $-40°$ C. for from 1 to 10 hours.

The addition $\underset{\sim}{11} \rightarrow \underset{\sim}{12}$ is accomplished by treating $\underset{\sim}{11}$ in a solvent such as tetrahydrofuran, diethylether, dimethoxyethane or the like at a temperature of from $-100°$ to 0° C. for from 15 minutes to 2 hours in the presence of $LiCH_2CO_2R^f$, wherein $R^f$ is benzyl, p-methoxybenzyl, 2,4-dimethoxybenzyl or the like; which reagent is typically generated in situ on treatment of the appropriate $R^f$ acetate with a strong base such as LDA, lithium hexamethyldisilazide, lithium 2,2,6,6-tetramethylpiperide, or the like.

If desired, a more readily removable carboxyl protecting group may conveniently replace the first established group, $R^f$, by the carboxyl protecting group $R^{2'}$. This transformation $\underset{\sim}{12} \rightarrow \underset{\sim}{13} \rightarrow \underset{\sim}{14}$ is accomplished by selectively deblocking $\underset{\sim}{12}$ to form $\underset{\sim}{13}$ by hydrogenation or hydrolysis. Typically, the reaction is accomplished by treating $\underset{\sim}{12}$ in a solvent such as methanol, ethanol, dioxane, tetrahydrofuran, water or the like under a hydrogenation pressure of from 1 to 4 atmospheres in the presence of a catalyst such as Pd on charcoal, $Pd(OH)_2$, or the like for from 0.1 to 10 hours. The $\underset{\sim}{13}$ intermediate (M may be H, Na, K or ammonium such as $Et_3NH$, for example) need not be isolated. Intermediate $\underset{\sim}{14}$ is obtained from the hydrogenation mixture upon treatment with the chosen reagent calculated to establish $R^{2'}$ such as an aralkyl halide in a solvent such as dimethylformamide, acetonitrile, hexamethylphosphoramide at a temperature of from 0° to 50° C. for from 0.5 to 18 hours. $R^7$ is typically an aralkyl group such as p-nitrobenzyl, or o-nitrobenzyl, for example.

The oxidation $\underset{\sim}{14} \rightarrow \underset{\sim}{15}$ is accomplished by treating $\underset{\sim}{14}$ in a solvent such as methylene chloride, acetonitrile, or the like with an oxidizing system such as dipyridine chromium (VI) oxide, 3,5-dimethylpyrazole chromium (VI) oxide, pyridinium chlorochromate, pyridinium dichromate, trifluoroacetic anhydride-dimethylsulfoxide, acetic anhydride-dimethyl sulfoxide or the like at a temperature of from $-78°$ C. to $25°$ C. for from 5 min. to 8 hrs.

Removal of protecting groups such as $R^{1'}$ (and others on $R^6$ or $R^7$) (15→16) is accomplished by acidic aqueous hydrolysis of 15 in a solvent such as methanol, ethanol, tetrahydrofuran, dioxane or the like in the presence of an acid such as hydrochloric, sulfuric, acetic or the like at a temperature of from 0° to 100° C. for from 2 to 18 hours.

The diazo species 17 is prepared from 16 by treating 16 in a solvent such as $CH_3CN$, $CH_2Cl_2$, THF, or the like, with an azide such as p-carboxybenzenesulfonylazide, toluenesulfonylazide, methanesulfonylazide, or the like, in the presence of a base such as triethylamine, pyridine, $(C_2H_5)_2NH$, or the like, for from 1 to 50 hours at 0°-25° C. (THF is tetrahydrofuran.)

Cyclization (17→18) is accomplished by treating 17 in a solvent such as benzene, toluene, THF, or the like, at a temperature of from 50°-110° C. for from 1-5 hours in the presence of a catalyst such as bis (acetylacetonato)Cu(II) [Cu(acac)$_2$], CuSO$_4$, Cu powder, Rh(OAc)$_2$, or Pd(OAC)$_2$. Alternatively, the cyclization may be accomplished by irradiating 6 through a pyrex filter (a wave length greater than 300 nm) in a solvent such as benzene, CCl$_4$, diethylether, or the like, at a temperature of from 0°-25° C. for from 0.5 to 2 hours. ["OAc"-=acetate.]

Establishment of leaving group X (18→19) is accomplished by acylating the keto ester 18 with an acylating agent R°X such as p-toluenesulfonic acid anhydride, p-nitrophenylsulfonic acid anhydride, 2,4,6-triisopropylphenylsulfonic acid anhydride, methanesulfonic acid anhydride, trifluoromethane sulfonic acid anhydride, diphenyl chlorophosphate, toluenesulfonyl chloride, p-bromophenylsulfonyl chloride, or the like; wherein X is the corresponding leaving group such as toluene sulfonyloxy, p-nitrophenylsulfonyloxy, diphenylphosphoryl, and other leaving groups which are established by conventional procedures and are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.1 to 5 hours. The leaving group X of intermediate 19 can also be halogen. The halogen leaving group is established by treating 18 with a halogenating agent such as $\phi_3PCl_2$, $\phi_3PBr_2$, $(\phi O)_3PBr_2$, oxalyl chloride or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The reaction 19→20 is accomplished by treating 19 in a solvent such as dioxane, dimethylformamide, dimethylsulfoxide, acetonitrile, hexamethylphosphoramide, or the like in the presence of an approximately equivalent to excess of the mercaptan reagent $HSR^8$, wherein $R^8$ is as defined above, in the presence of a base such as sodium hydrogen carbonate, potassium carbonate, triethylamine, diisopropylethylamine, or the like at a temperature of from −40° to 25° C. for from 1 to 72 hours. When $R^8$ is substituted by a primary or secondary amino group, for example —$CH_2CH_2NH_2$, the mercaptan reagent may be represented as $HSCH_2CH_2NHR°$, for example; wherein R° is a readily removable N-protecting group such as p-nitrobenzyloxycarbonyl, (—CO$_2$PNB), o-nitrobenzyloxycarbonyl, or the like. The specifically illustrated mercaptan reagent, $HSCH_2CH_2NHR°$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours. The foregoing mercaptan reagent, $HSR^8$, and means for its protection, is simply illustrative. The class of suitable $HSR^8$ reagents is representatively described below and in the Examples.

The final deblocking step 20→I is accomplished by conventional procedures such as solvolysis or hydrogenation. Typically 20 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.25 to 4 hours to provide I. Photolysis, when $R^{2'}$ is a group such as o-nitrobenzyl, for example, may also be used for deblocking.

Introduction of the Thia Side Chain

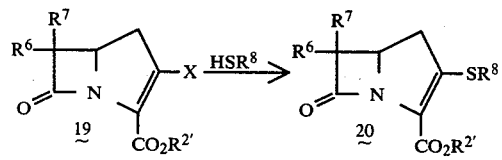

Relative to the foregoing description of the invention, suitable reagents $HSR^8$ utilized in the transformation 19→20 are listed below. The list is arranged according to structural and functional characteristics of the thia side chain —$SR^8$; annotation is provided where necessary. The thia side chain of choice is derived from the corresponding mercaptan reagent $HSR^8$. When the mercaptan contains a functional group which might interfere with the intended course of reaction, the offending group is covered. For example, when a basic nitrogen group is encountered (—NHR or —NH$_2$, for example) it is usually protected by acylation (e.g., —CO$_2$PNB) and when a carboxyl group (—CO$_2$H) is present, it is usually protected by esterification (e.g., PNB ester). Such protection also facilitates in the purification of products 20 by chromatographic means. (PNB is p-nitrobenzyl).

(1) Aliphatic (including carbocyclic) Mercaptans: $HSR^8$ wherein $R^8$ is 1–10 carbon alkyl, cycloalkyl, alkenyl, cycloalkenyl, or alkynyl; $R^8$ may be branched or unbranched,

EXAMPLES

HSCH$_3$
HSCH$_2$CH$_3$
HSCH$_2$CH$_2$CH$_3$
HSCH(CH$_3$)$_2$
HS(CH$_2$)$_3$CH$_3$
HS—CH—CH$_2$CH$_3$
　　　|
　　　CH$_3$
HSCH$_2$CH(CH$_3$)$_2$
　　CH$_3$
　　　|
HS—C—CH$_3$
　　　|
　　CH$_3$

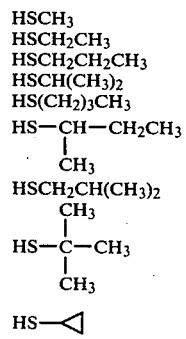

-continued

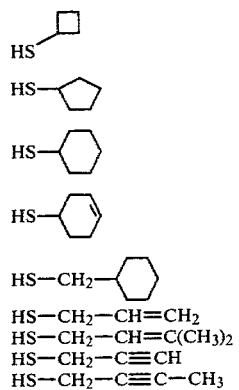

HS—CH₂—CH=CH₂
HS—CH₂—CH=C(CH₃)₂
HS—CH₂—C≡CH
HS—CH₂—C≡C—CH₃

(2) Substituted Aliphatic Mercaptans: HSR⁸ wherein R⁸ is a 1-10 carbon branched or unbranched alkyl, cycloalkyl, alkenyl, cycloalkenyl or alkynyl group substituted by one or more halo, OH, OR¹, $$\overset{O}{\underset{\|}{OCR^1}}, \overset{O}{\underset{\|}{OCNH_2}}, \overset{O}{\underset{\|}{OCNR^1R^2}},$$

NH₂, NHR¹, NR¹R², $$\overset{O}{\underset{\|}{CR^1}},$$

CO₂H, CO₂R¹, CONH₂, CONHR¹, CONR¹R², CN, SR¹, $$\overset{O}{\underset{\|}{SR^1}},$$

SO₂R¹, SO₂NH₂, SO₂NHR¹, SO₂NR¹R², $$\overset{O}{\underset{\|}{NHCR^1}}, \overset{O}{\underset{\|}{NHCNH_2}}, \overset{O}{\underset{\|}{NHCNHR^1}},$$

$$\overset{O}{\underset{\|}{NHCNR^1R^2}}, \overset{O}{\underset{\|}{NHCOR^1}}, \overset{NH}{\underset{\|}{CNH_2}}, \overset{NR^1}{\underset{\|}{CNHR^2}},$$

wherein R¹ and R² are as previously defined relative to substituents on R⁸. Preferred substituents are basic nitrogen containing groups.

EXAMPLES

HS(CH₂)ₙOR¹ n = 2-4, R¹ = H, $\overset{O}{\underset{\|}{CCH_3}}$, CH₃

HS(CH₂)ₙCXR
n = 1-3, X = O, NH, NR¹ R¹ = H, CH₃
HS(CH₂)ₙNH₂
n = 2-4
HS(CH₂)ₙNHR¹ n = 2-4, R¹ = CH₃, CH₂CH₃, CH₂CH₂CH₃, $\overset{O}{\underset{\|}{CCH_3}}$
HS(CH₂)ₙNR¹R²
n = 2-4, R¹/R² = CH₃, CH₂CH₃

HS—CH—CH₂NH₂
　　|
　　CH₃

-continued

HS—C(CH₃)₂—CH₂NH₂ (with CH₃ groups)

HS—CH₂—CH(CH₃)—NH₂

HS—CH₂—C(CH₃)₂—NH₂

HS—CH₂CH₂SCH₃
HS—CH₂CH₂NHC(CH₃)₃

HS—CH₂—C(CH₃)₂—CH₂NHR¹

R¹ = H, CH₃, $\overset{O}{\underset{\|}{CCH_3}}$

HS—CH₂CH₂—NH—C₆H₁₁ (cyclohexyl)

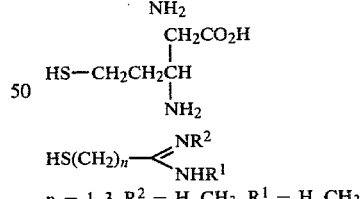

n = 3-5

HS—CH(CH₂NR¹R²)—CH₂NR¹R²
R¹ = H, CH₃; R² = H, CH₃

HS—CH₂—CH(NHR¹)—CH₂NHR¹
R¹ = H, CH₃

HS—CH₂—CH(OH)—CH₂NH₂

HS—CH₂—CH(CH₂NH₂)—CH₂NH₂

HS—CH₂—CH(CO₂H)—NH₂

HS—CH₂—CH(CO₂H)—CH₂—NH₂

HS—CH₂—CH(NH₂)—CH₂—CO₂H

HS—CH₂CH₂—CH(CH₂CO₂H)—NH₂

HS(CH₂)ₙ—C(=NR²)(NHR¹)

n = 1-3, R² = H, CH₃, R¹ = H, CH₃

HS—CH=CH—NHC(O)CH₃

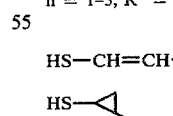

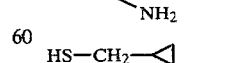

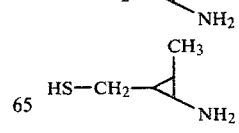

HS—(cyclobutyl)—NH₂

-continued

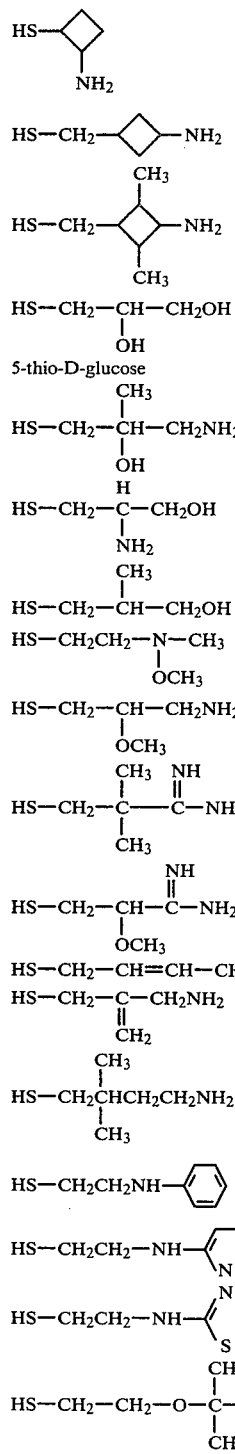

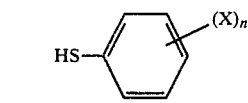

n = 1, 2 or 3,

X = F, Cl, Br, OH, OR, OCR$^1$, NH$_2$,
NHR$^1$, NR$^1$R$^2$, CH$_2$NH$_2$, CH$_2$NR$^1$R$^2$, CO$_2$H,
CO$_2$R$^1$, COR$^1$, CONH$_2$, CONR$^1$R$^2$, R$^1$CONH,
R$^1$NHCONH, SR$^1$, $\overset{O}{\underset{\|}{S}}$R$^1$, SO$_2$R$^1$, CH$_3$, CF$_3$;
R$^1$ and R$^2$ are as previously defined
under R$^8$.

EXAMPLES

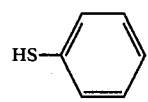

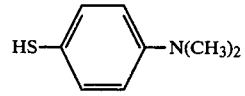

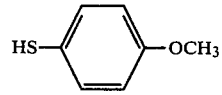

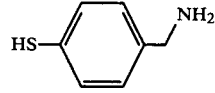

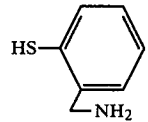

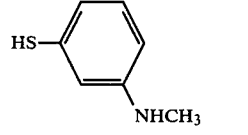

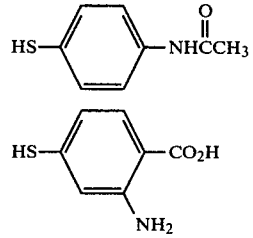

(3) Aryl Mercaptans: HSR$^8$ wherein R$^8$ is phenyl or substituted phenyl. The substituents are independently selected from those previously defined for R$^8$. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

(4) Heteroaryl Mercaptans: HSR$^8$ wherein R$^8$ is a substituted or unsubstituted heteroaryl group containing 1-4 O, N or S atoms. Typical substituents include those mentioned above under "Aryl Mercaptans".

EXAMPLES

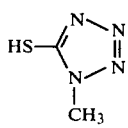

-continued

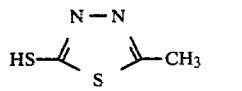

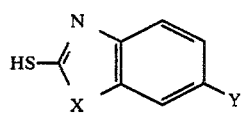

X = N,O Y = H
X = S Y = H,
Cl, OCH₂CH₃

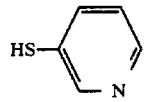

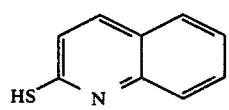

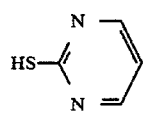

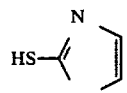

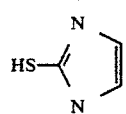

R = H, CH₃

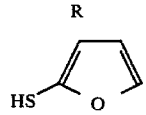

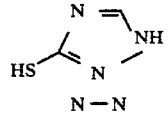

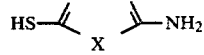

X = NH, S

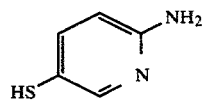

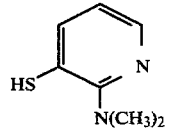

(5) Arylaliphatic Mercaptans: $HSR^8$ where $R^8$ is a 1-6 carbon branched or unbranched alkyl, cycloalkyl, alkenyl, or alkynyl group substituted by a phenyl or substituted phenyl group. Typical phenyl substituents include those mentioned under "Aryl Mercaptans".

EXAMPLES

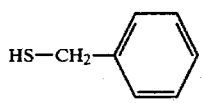

-continued

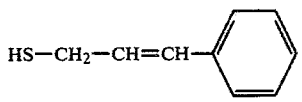

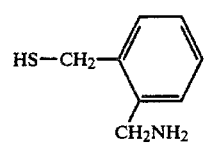

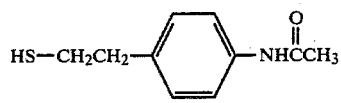

(6) Heteroarylaliphatic and Heterocyclicaliphatic Mercaptans $HSR^8$ wherein $R^8$ is a 1-6 carbon branched or unbranched alkyl, cycloalkyl, alkenyl, or alkynyl group substituted by a heteroaryl or heterocyclic group containing 1-4, O, N, or S atoms. The heteroaryl or heterocyclic group is unsubstituted or substituted by those substituents mentioned under "Aryl Mercaptans", (No. 3, above).

EXAMPLES

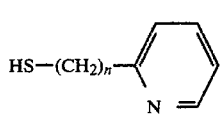

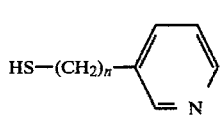

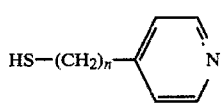

n = 1,2

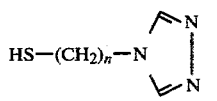

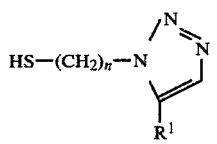

$R^1$ = OCH₂CH₃

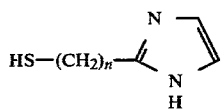

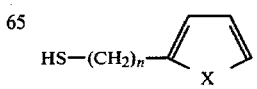

-continued
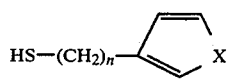
X = O, S, NH
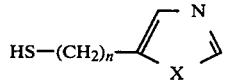
X = O, S, NH
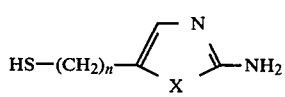
X = O, S, NH
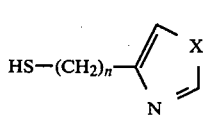
X = O, S, NH
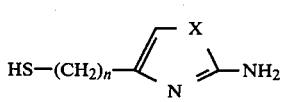
X = O, S, NH
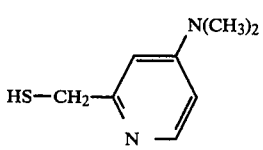
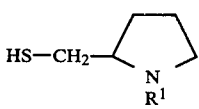
R¹ = H, CH₃
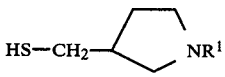
R¹ = H, CH₃
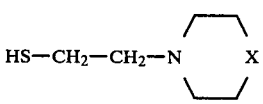
X = O, NH, NCH₃
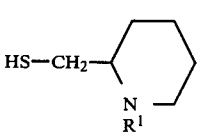
R¹ = H, CH₃
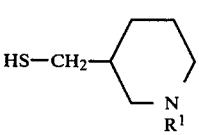
-continued
R¹ = H, CH₃
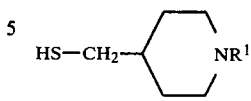
R¹ = H, CH₃
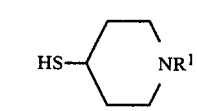
R¹ = H, CH₃
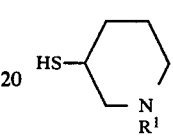
R¹ = H, CH₃
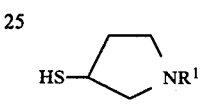
R¹ = H, CH₃
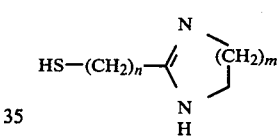
n = 1-3, m = 1-3
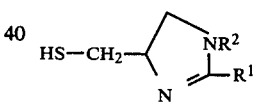
R² = H, CH₃, R¹ = H, CH₃, NH₂
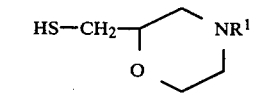
R¹ = H, CH₃
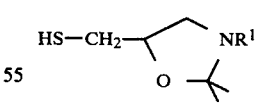
R¹ = H, CH₃
(7) Alkyl-Heteroatom-Alkyl Mercaptans, HSR⁸: wherein R⁸ is
—(CH₂)$_n$X(CH₂)$_m$R⁹
wherein n=2 to 4, m=2 to 4; X is NR°, O or S; and wherein R° is H, CH₃, CH₂CH₃, CH₂CH₂OH, or CH₂CH₂NH₂ and R⁹ is OH, NH₂, NHCH₃, N(CH₃)₂,

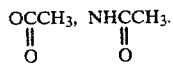

Note, in the above representation, the methylene carbons may be branched; for example:

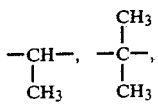

and the like.

The following HSR⁸ are representative of this class:

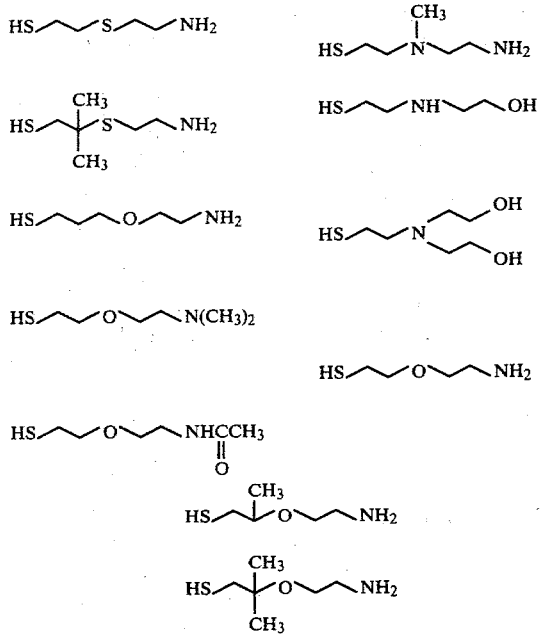

As noted above, the compounds of the present invention may also generally be represented by the following structural formula:

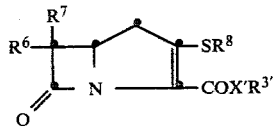

wherein X' is oxygen, sulfur or NR' (R' is hydrogen or loweralkyl having from 1 to 6 carbon atoms); and $R^{3'}$ is hydrogen, or, inter alia, is representatively selected to provide the pharmaceutically acceptable salt, ester anhydride ($R^{3'}$ is acyl) and amide moieties known in the bicyclic β-lactam antibiotic art; $R^{3'}$ may also be a readily removable blocking group.

Identification of the Radical —COX'R³'

In the generic representation of the compounds of the present invention (I, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and nuclear analogues thereof.

Suitable blocking esters (R³', X'=O) include those selected from the following list which is representative:

(i) $R^{3'}=CR^aR^bR^c$ wherein at least one of $R^a$, $R^b$ and $R^c$ is an electron-donor, e.g., p-methoxyphenyl. The remaining $R^a$, $R^b$ and $R^c$ groups may be hydrogen or organic substituting groups. Suitable ester groups of this type include p-methoxybenzyloyxcarbonyl.

(ii) $R^{3'}=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula:

$$R^4{}_3SiX'$$

wherein X' is a halogen such as chloro or bromo and $R^4$ is alkyl, e.g., methyl, ethyl, t-butyl.

Pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkyl portion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the $$\begin{matrix} R' \\ -N- \end{matrix} \text{ group.}$$

Representative of such amides are those wherein R' is selected from the group consisting of hydrogen and lower alkyl such as methyl and ethyl.

The most preferred —COX'R³' radicals of the present invention are those wherein (relative to Structure I above), X' is oxygen and R³' is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia coli, Klebsiella pneumoniae, Bacillus subtilis, Salmonella typhosa, Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above schematic reaction diagram for the total synthesis of the defined carbapenem antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

Preparation of 4(S)-4-Iodomethylazetidin-2-one

STEP A

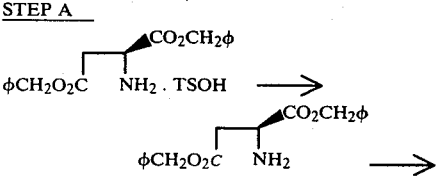

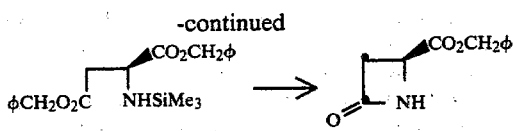

Benzyl (S)-azetidin-2-one-4-carboxylate

To a 1000 ml separatory funnel are added dibenzyl (S)-aspartate p-toluenesulfonic acid salt (48.6 g, 0.1 mole), ice-cold diethyl ether (300 ml), ice-cold water (100 ml), and ice-cold saturated aqueous potassium carbonate (50 ml). The mixture is shaken vigorously and the layers are separated. The aqueous portion is extracted with more cold diethyl ether (2×100 ml). The combined ether solution is washed with brine, dried with magnesium sulfate, and evaporated under vacuum to provide dibenzyl (S)-aspartate (31.4 g, 0.1 mole) as a colorless liquid The dibenzyl (S)-aspartate in anhydrous diethyl ether (200 ml) is cooled in an ice-bath under a nitrogen atmosphere. Trimethylchlorosilane (12.7 ml, 0.1 mole) is added to the stirred solution to give a white precipitate. Triethylamine (14.0 ml, 0.1 mole) is then added to the mixture. The cooling bath is removed and the mixture is stirred at room temperature (22°–25° C.) for 2 hrs. The mixture is then filtered directly into a 3-neck, 1.0 liter, round bottom flask fitted with a sintered glass funnel, magnetic stirrer, and a vacuum-nitrogen inlet. This operation is carried out under a blanket of nitrogen, care being taken to exclude atmospheric moisture. The sintered glass funnel is replaced by a stopper and the ether is evaporated under vacuum with stirring to provide dibenzyl (S)-N-trimethylsilylaspartate (35.5 g, 0.092 mole) as a slightly hazy oil.

Anhydrous diethyl ether (250 ml) is added to the flask containing the silyl derivative and the magnetic stirrer is replaced by a mechanical stirrer. The resulting solution is stirred under a nitrogen atmosphere with ice-bath cooling. Ethereal ethyl magnesium bromide (34 ml of a 2.94 M solution, 0.1 mole) is added dropwise over 40 min. to give a cream colored, stirable precipitate. The cooling bath is removed and the mixture is stirred at room temperature. After 1.5 hrs, a viscous gum forms. The mixture is allowed to stand overnight at room temperature. The mixture is then cooled in an ice-methanol bath while ammonium chloride saturated 2 N hydrochloric acid (100 ml) is added slowly with stirring. The resulting mixture is diluted with ethyl acetate (100 ml) and water (100 ml) and the layers are separated. The aqueous portion is extracted with more ethyl acetate (3×100 ml). The combined organic solution is washed with water (200 ml), 5% aqueous sodium bicarbonate solution (100 ml), water (100 ml), and brine, dried with magnesium sulfate, and filtered. Evaporation of the solvent under vacuum gives an orange oil interspersed with a fine, granular precipitate (25.3 g). This material is dissolved in warm chloroform (75 ml), diluted with petroleum ether (125 ml), seeded, scratched, and cooled in an ice-bath. The precipitate is collected, washed with petroleum ether, and dried under vacuum to give benzyl (S)-azetidin-2-one-4-carboxylate (3.85 g) as an off-white solid mp 136°–139° C. The mother liquors and washings are combined, diluted with petroleum ether to 500 ml, seeded, and left in a refrigerator for several days. The resulting precipitate is collected, washed with petroleum ether, and dried under vacuum to give additional product (0.82 g) as pale yellow crystals. Recrystallization of a sample from chloroform-petroleum ether gave the product as small, white flakes: mp 141°–143°; $[\alpha]_D = -43.4°$ (c3.275 in $CHCl_3$); IR($CHCl_3$) 3425, 1778, 1746 $cm^{-1}$; $^1H$ NMR($CDCl_3$) δ 3.00 (ddd, 1, J=1.9, 3.2, and 14.6 Hz, H-3a), δ 3.35 (dd, 1, J=1.5, 5.4, and 14.6 Hz, H-3b), δ 4.20 (dd, 1, J=3.2 and 5.4 Hz, H-4), δ 5.22 (s, 2, $OCH_2Ph$), δ 6.48 (m, 1, NH), 7.38 (s, 5, phenyl); mass spectrum m/e 205 (M+), 163, 91, 70, 43.

Anal. Calcd. for $C_{11}H_{11}NO_3$: C, 64.38; H, 5.40; N, 6.83. Found: C, 64.10; H, 5.70; N, 6.77.

STEP B

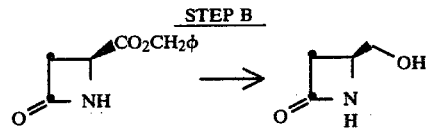

4(S)-4-Hydroxymethylazetidin-2-one

Sodium borohydride (3.69 g, 97.5 mmol) is added in one portion to a suspension of benzyl 4(S)-azetidin-2-one-4-carboxylate (20.0 g, 97.5 mmol) in 300 ml of absolute methanol at 0° C. The mixture is then allowed to warm slowly with periodic cooling being supplied to keep the internal temperature <30° C. After stirring for 2 hr., glacial acetic acid (23.4 g, 390 mmol) is added and the reaction mixture is concentrated under vacuum. The residue is treated with 500 ml of chloroform and filtered. The filtrate is concentrated under vacuum and the residue is chromatographed on 250 g of silica gel (4:1, chloroform: methanol) to yield 9.62 g (98%) of 4(S)-hydroxymethylazetidin-2-one as a white solid: m.p. 51°–53° C.; $[\alpha]_D = +68.0°$ (C=2.676 in $CHCl_3$); IR ($CHCl_3$) 3410, 1765 $cm^{-1}$ $^1H$ NMR ($CDCl_3$) δ 7.07 (1H, br. s, NH), δ 4.05 (1H, br. s, OH), δ 3.77 (2H, m H4, H-5a or b), δ 3.58 (1H, dd, J=11, 6, H-5a or b), δ 2.97 (1H, ddd, J=14.5, 4.8, 1.3, H3b), δ 2.7 (1H, br. d, J=14.5, H3a); mass spectrum m/e 101 (M+), 83.

STEP C

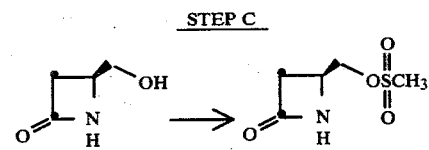

4(S)-4-Methanesulfonyloxymethyl azetidin-2-one

Methane sulfonyl chloride (11.46 g, 100 mmol) is added dropwise by syringe to a solution of 4(S)-4-hyroxymethyl azetidin-2-one (10.1 g, 100 mmol) and triethyl amine (10.1 g, 100 mmol) in 15 ml of dry methylene chloride at 0° C. (Warming is necessary in order to initially solubilize the alcohol. The resulting solution is then cooled to 0° C. prior to addition of the other reagents). The resulting solution is stirred at 0° C. for 1 hr. during which time a voluminous precipitate is produced. At the end of this time, the reaction mixture is filtered and the filtrate is concentrated under vacuum. The two solid residues are combined and treated with 500 ml of chloroform. The resulting mixture is filtered to yield substantially pure 4(S)-4-methanesulfonyloxymethyl azetidin-2-one as a white solid. The filtrate, which contains most of the triethylamine hydrochloride, is concentrated under vacuum and chromatographed on 200 g of silica gel (4:1 chloroform:methanol) to yield an additional quantity of mesylate. This material is combined with that obtained previously and recrystallized from chloroform to yield 15.57 g (87%) of 4(S)-4-methanesulfonyloxymethylazetidin-2-one as colorless needles: m.p. 109.5°–110.5° C.; $[\alpha]_D = +25.8°$ (C=1.025 in H$_2$O);

NMR (D$_2$O) δ 4.62 (1H, dd, J=11.2, 3.0, H-5a or b), δ 4.43 (1H, dd, J=11.2, 6, H-5a or b), δ 4.12 (1H, m, H4)

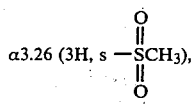

α3.26 (3H, s —SCH$_3$),

δ 3.19 (1H, dd, J=15, 4.5, H3b).

δ 2.88 (1H, dd, J=15, 2.5, H3a); mass spectrum m/e 179 (M+), 136;

Anal: Calc: C, 33.51; H, 5.06; N, 7.82; S, 17.89. Found: C, 33.54; H, 5.08; N, 7.72; S, 17.93.

STEP D

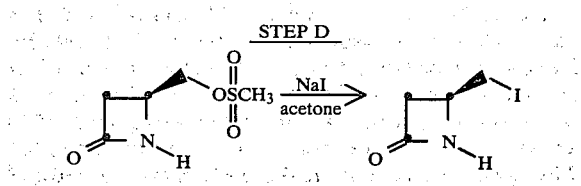

4(S)-4-Iodomethylazetidin-2-one

A mixture of 4(S)-4-methanesulfonyloxy azetidin 2-one (11.8 g, 65.9 mmol) and powdered sodium iodide (19.8 g, 132 mmol) in 130 ml of acetone is heated at reflux for 6 hr. The resulting reaction mixture is concentrated in vacuo, treated with 200 ml of chloroform and filtered. The filtrate is washed with 2×50 ml of water and dried over magnesium sulfate. The organic phase is filtered, concentrated in vacuo, and chromatographed on 250 g of silica gel (ethyl acetate) to yield 11.94 g (86%) of 4(S)-4-iodomethyl-azetidin-2-one as a white solid. This material is recrystallized from ether-petroleum ether to yield white crystals: mp 91°–92° C.; $[\alpha]_D = -23.7°$ (C=1.354 in CHCl$_3$); IR (CHCl$_3$) 3450, 1765 cm$^{-1}$, 1H NMR (CHCl$_3$) δ 6.13 (brs, N—H), δ 3.94 (m, 1H, Hc), δ 3.36 (m, 2H, Hd and e), δ 3.16 (ddd, 1H, J=14.9, 5.4, 2.3, Ha), δ 2.72 (d, d, d, 1H, J=14.9, 2.1, 2, Hb) mass spectrum m/e 211 (M+), 168, 142, 127, 84.

EXAMPLE 2

Preparation of (4S)-1-(t-Butyldimethylsilyl)-4-iodomethylazetidin-2-one

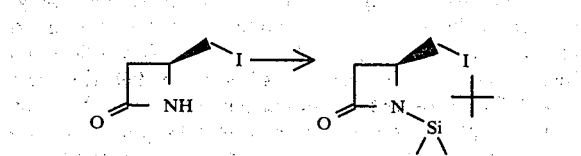

t-butyldimethylchlorosilane (7.51 g, 49.8 mmol) is added in one portion to an ice-cold, stirring solution of (4S)-4-iodomethyl-azetidin-2-one (10.0 g, 47.4 mmol) and triethylamine (5.04 g, 49.8 mmol) in anhydrous dimethylformamide (100 ml). A voluminous white precipitate forms almost immediately. The reaction mixture is stirred at 0°–5° for 1 hour and then allowed to warm to room temperature. Most of the solvent is removed under vacuum to give a residue which is partitioned between diethyl ether (250 ml) and water. The ethereal phase is washed with 2.5 N hydrochloride acid (50 ml), water (3×50 ml), and brine, dried with magnesium sulfate, filtered, and evaporated under vacuum to provide (4S)-1-(t-butyldimethylsilyl)-4-iodomethyl-azetidin-2-one (15.1 g) as a white solid. Recrystallization from petroleum ether-ethyl ether gives the product as colorless plates, mp 71°–72°; n.m.r. (CDCl$_3$), δ 3.8 (m,l), δ 2.6–3.6 (2 overlapping d of AB, 4) δ 1.0 (S,9), δ 0.3(S,6), δ 0.25(S,6).

EXAMPLE 3

Preparation of (4S)-1-(t-Butyldimethylsilyl)-4-(2,2,2-tri(methylthio)-ethyl)azetidin-2-one

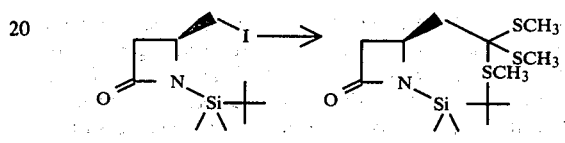

n-Butyllithium (19.4 ml of 2.5 M hexane solution, 48.5 mmol) is added slowly by syringe to a solution of tri(-methylthio)methane (7.47 g, 48.5 mmol) in 150 ml of freshly distilled THF at −78° C. The resulting solution is stirred at −78° C. for 30 min. prior to the addition of a solution of (4S)-1-(tert-butyldimethylsilyl)-4-iodomethylazetidin-2-one (15.0 g, 46.15 mmol) in 50 ml of THF. This solution is stirred at −78° C. for 30 min., then quenched by addition of saturated aqueous ammonium chloride solution. The reaction mixture is allowed to warm to room temperature, then poured into ether (250 ml), washed with water (2×100 ml) brine (100 ml) and dried over magnesium sulfate. Removal of solvents in vacuo gives an oil which is crystallized from petroleum ether to give 13.3 g (82%) of (4S)-1-(t-butyldimethylsilyl)-4-(2,2,2-tri(methylthio)ethyl)azetidin-2-one as colorless prisms. m.p. 61°–62° C. IR(CHCl$_3$, CM$^{-1}$) 2918, 2850, 1730; n.m.r. (CDCl$_3$) δ 4.0(m,l), δ 3.35(dd,l,J=5.5,16), δ 2,83 (dd,l,J=3,16) δ 2,5(ABq,2) δ 2,15(s, 9), δ 0.98(s,9), δ0.25(s,6).

EXAMPLE 4

Preparation of (3S, 4R)-1-(t-butyldimethylsily)-3-[(R)-1-hydroxyethyl]-4-[2,2,2-tri(methylthio)ethyl]azetidin-2-one

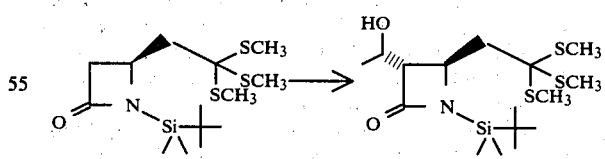

n-Butyllithium (14.8 ml of 2.5 N hexane solution, 37.0 mmol) is added by syringe to a solution of diisopropylamine (3.74 g, 37.0 mmol) in 180 ml of freshly distilled tetrahydrofuran at −78° C. The resulting solution is stirred at −78° C. for 15 min prior to the addition of a solution of (4S)-1-(t-butyldimethylsilyl)-4-[2,2,2-tri(methylthio)ethyl]azetidin-2-one (12.34 g, 35.16 mmol) in 35 ml of tetrahydrofuran. This solution is stirred at −78° C. for 10 min prior to the addition of acetaldehyde (4.62 g, 105 mmol). The solution is stirred for an additional 5 min. at −78° C. and then quenched by addition of saturated aqueous ammonium chloride solution, and allowed to warm to room temperature. The mixture is poured into 250 ml of ether and washed with water (2×100 ml) and brine and dried over magnesium sulfate. Removal of solutions in vacuo gives an oil which is chromatographed on a silica gel column (1:1 ether: petroleum ether) to give (3S,4R)-1-(t-butyldimethylsilyl)3-[(R)-1-hydroxyethyl]-4-[2,2,2-tri(methylthio)ethyl]azetidin-2-one (7.0 g, 50.4%) at $R_f$=0.2. The product can be recrystallized from petroleum ether. Alternatively, the trans R product can be isolated from the crude reaction mixture by direct crystallization from a petroleum ether solution.

EXAMPLE 5

Preparation of (3S,4R)-1-(t-Butyldimethylsilyl)-3-(1-oxoethyl)-4-[2,2,2,-tri(methylthio)ethyl]azetidin-2-one

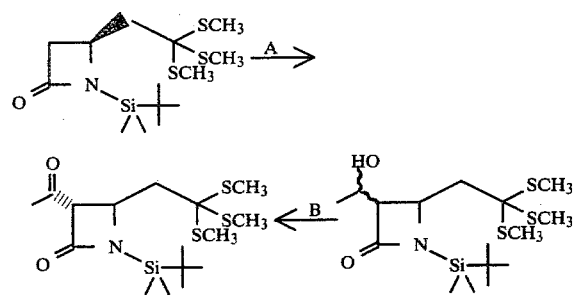

A. n-Butyllithium (2.43 ml of 2.4 m solution, 5.84 mmol) is added by syringe to a solution of diisopropylamine (591 mg, 5.84 mmol) in 25 ml of freshly distilled tetrahydrofuran at −78° C. The resulting solution is stirred at −78° C. for 15 minutes prior to the addition of a solution of (4R)-1-(t-butyldimethylsilyl)-4-[2,2,2-tri(-methylthio) ethyl]azetidin-2-one (1.00 g, 2,85 mmol) in tetrahydrofuran (5 ml). This solution is stirred at −78° C. for 15 minutes, then added via a Teflon tube to a mixture of N-acetylimidazole (642 mg. 5.84 mmol) in 25 ml of THF at −78° C. The resulting yellow reaction mixture is stirred at −78° C. for 10 minutes, then quenched by addition of saturated aqueous ammonium chloride solution. The mixture is diluted with ether (200 ml) and washed with 2.5 N hydrochloric acid solution (50 ml), water (50 ml) and brine (50 ml) and dried over magnesium sulfate. Removal of solvents in vacuo gives a yellow oil which is chromatographed on silica gel (30% ether in petroleum ether) to yield (3S, 4R)-1-(t-butyldimethylsilyl)-3-(1-oxoethyl)-4-[2,2,2-tri(methylthio)ethyl]azetidin-2-one. n.m.r. (CDCl₃) δ 4.42(m,1), δ 4.32(d,1) δ 2.35(m,2), δ 2.32(s,3), δ 2.2(s,9), δ 0.98(s,9), δ 0.3(2s,6).

B. Trifluoroacetic anhydride (400 mg., 1.905 mmol) is added by syringe to a solution of dimethyl sulfoxide (2.53 mmol) in dry methylene chloride (5 ml) at −78° C. The resulting mixture is stirred at −78° C. for 30 minutes prior to the addition of a solution of (3RS, 4R)-1-(t-butyldlimethylsilyl)-3-[(RS)-1-hydroxyethyl]-4-[2,2,2-tri(methylthio)ethyl]azetidin-2-one (500 mg., 1.27 mmol) in dry CH₂cl₂(1 ml). The resulting solution is stirred for 30 minutes prior to the addition of triethylamine (360 mg., 3.56 mmol). The cooling bath is removed. After 40 minutes, the reaction mixture is diluted with CH₂Cl₂, washed with water and brine and dried over magnesium sulfate. Removal of solvents in vacuo gives an oil which is purified as above. Yields 432 mg. (86%).

EXAMPLE 6

Preparation of (3S,4R)-1-(t-butyldimethylsilyl)-3-[(R)-1-hydroxyethyl]-4-[2,2,2-tri(methylthio)ethyl]azetidin-2-one

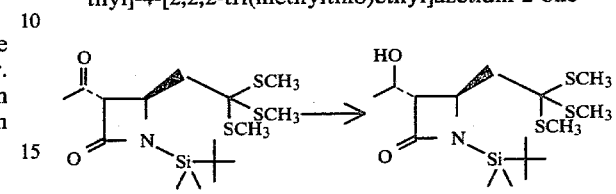

K-Selectride ® (3.64 ml of 0.5 M, 1.82 mmol) is added by syringe to a mixture of potassium iodide (126 mg., 0.758 mmol) and (3S,4R)-1-(t-butyl dimethylsilyl)-3-(1-oxoethyl)-4-[2,2,2-tri(methylthio)ethyl]azetidin-2-one (298 mg, 0758 mmol) in freshly distilled ethyl ether (8 ml) at room temperature. The resulting mixture is stirred at room temperature for 2.5 hours, then quenched by the addition of acetic acid (218 mg., 3.64 mmol). The resulting mixture is diluted with ethyl acetate (25 ml) and filtered through celite. Removal of solvents in vacuo gives an oil which is chromatographed on silica gel (ether:petroleum ether) to yield 252 mg of (3S, 4R)-1-(t-butyldimethylsilyl)-3-[(R)-1-hydroxyethyl]4-[2,2,2-tri(methylthio) ethyl]azetidin-2-one. N.M.R. (R isomer, CDCl₃+D₂O) δ 4.15(dq,1), δ 3.95(ddd,1,J=9.5,2.3), δ 3.26(dd,1,J=8,2.3), δ 2.37(m,2), δ 2.16(s,9), δ 1.37(d,3,J=6,6), δ 1.0(s,9), δ 0.26(s,6).

EXAMPLE 7

Preparation of (3S,4R)-1-(t-Butyldimethylsilyl)-3-((R)-1-hydroxyethyl)-4-carbomethoxymethylazetidin-2-one.

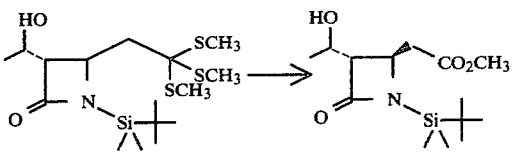

Mecuric chloride (12.37 g, 45.6 mmol) is added in one portion to a solution of (3S,4R)-1-(t-butyldimethylsilyl)-3-[(R)-1-hydroxyethyl]-4-[2,2,2-tri(methylthio)ethyl] azetidin-2-one (6.0 g, 15.2 mmol) in 250 ml of absolute methanol at 0° C. The resulting mixture (heavy white precipitate) is stirred at 0° C. for 3 min., then quenched by addition of sodium bicarbonate (8.99 g, 107 mmol). This mixture is then filtered and the solid residue is washed with additional methanol. The combined filtrate and washings are concentrated in vacuo and the residue is partitioned between ethyl acetate and saturated aqueous ammonium chloride solution. The organic phase is separated, washed with saturated aqueous ammonium chloride solution, water and brine and dried over magnesium sulfate. Removal of solvents in vacuo gives an oil which is chromatographed on a silica gel column (3:2 cyclohexane:ethyl acetate) to yield (3S, 4R)-1-(t-butyldimethylsilyl)-3-[(R)-1-hydroxyethyl)]-4-carbomethoxymethyl azetidin-2-one.

EXAMPLE 8

Preparation of
(3S,4R)-1-(t-Butyldimethylsilyl)-3-[(R)-1-(t-butyldimethylsilyloxy)ethyl]-4-carbomethoxymethylazetidin-2-one

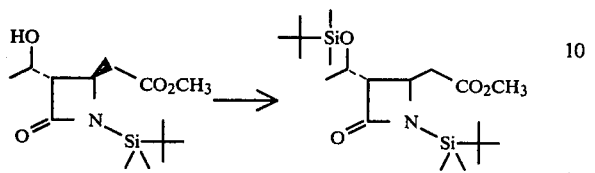

t-Butyldimethylchlorosilane (940 mg, 6.25 mmol) is added in one portion to a solution of (3S, 4R)-1-(t-butyldimethylsilyl)-3-[(R)-1-hydroxyethyl]-4-carbomethoxymethylazetidin-2-one (1.88 g, 6.25 mmol) and triethylamine (1.27 g, 6.25 mmol) in 15 ml of anhydrous dimethylformamide at 0° C. After 15 min. at 0° C. the cooling bath is removed and the reaction mixture is stirred at room temperature for 24 hrs. Ether (100 ml) is added and the mixture is filtered, then washed with 2.5 N hydrochloric acid (20 ml), water (3×20 ml) and brine. The organic phase is dried over magnesium sulfate, then concentrated in vacuo. The residue is chromatographed on silica gel (7:3 petroleum ether:ether) to yield (3S, 4R)-1-(t-butyldimethylsilyl)-3-[(R)-1-(t-butyldimethylsilyloxy)ethyl]-4-carbomethoxymethylazetidin-2-one. n.m.r. (CDCl$_3$)δ4.1(m,2), δ3.68(S,3), δ3.03(dd,1,J=4.3,2.7), δ2.8(ABq,2), δ1.17(d,3,J=6.6), δ0.98(s,9), δ0.89(s,9), δ0.23(s,6), δ0.1(s,6).

EXAMPLE 9

Preparation of
(3S,4R)-1-(t-Butyldimethylsilyl)-3-[(R)-1-(t-butyldimethylsilyloxy)ethyl]-4-(2-oxoethyl)azetidin-2-one

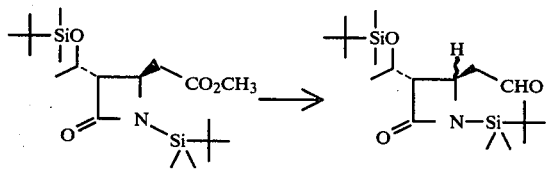

Diisobutylaluminum hydride (3.72 ml of 0.91 M in hexane, 3.38 mmol) is added slowly by syringe to a solution of (3S, 4R)-1-(t-butyldimethylsilyl)-3-[(R)-1-(t-butyldimethylsilyloxy)ethyl]-4-carbomethoxymethyl azetidin-2-one (936 mg, 2.26 mmol) in 25 ml of freshly distilled toluene at −78° C. The resulting solution is stirred at −78° C. for 3 hrs., then quenched by addition of 2.5 N hydrochloric acid (5 ml). The resulting mixture is stirred for 2 min., then poured into a separatory funnel containing 100 ml of ether and 50 ml of 1.25 N hydrochloric acid saturated with tartaric acid. The organic phase is separated and the aqueous phase is extracted with ether (2×50 ml). The combined organic phases are washed with brine and dried over magnesium sulfate. Removal of solvents in vacuo gives a white solid which is recrystallized from ether-petroleum ether to give (3S,4R)-1-(t-butyldimethylsilyl)-3-[(R)-1-(t-butyldimethylsilyloxy)ethyl]-4-(2-oxoethyl)-azetidin-2-one. m.p. 115°–116° C.; n.m.r. (CDCl$_3$) δ4.1(m,1), δ4.03(m,1), δ2.7–3.2(m,3), δ1.23(d,3,J=6.4), δ1.08(s,9), δ0.9(s,9), δ0.25(s,6), δ0.1(s,6), δ9.83(t,1,J=1.4).

EXAMPLE 10

Preparation of
(3S,4R)-1-(t-Butyldimethylsilyl)-3-[(R)-1-(t-butyldimethylsilyloxy)ethyl]-4-(3-benzyloxycarbonyl-2-hydroxypropyl)azetidin-2-one

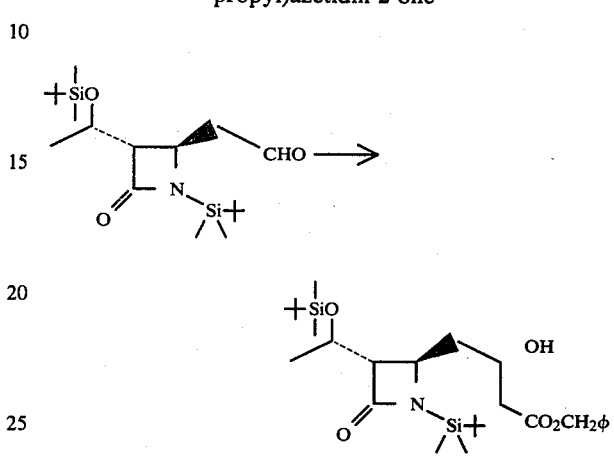

n-Butyllithium (1.81 mmol) is added by syringe to a solution of diisopropylamine (1.81 mmol) in 9 ml of freshly distilled tetrahydrofuran at −78° C. The resulting solution is stirred for 15 min at −78° C. Benzyl acetate (1.81 mmol) is then added dropwise by syringe and the resulting solution is stirred at −78° C. for 20 min. A solution of (3S, 4R)-1-(t-butyldimethylsilyl)-3-[(R)-1-(t-butyldimethylsilyloxy)ethyl]-4-(2-oxoethyl)azetidin-2-one (1.64 mmol) in 3 ml of anhydrous tetrahydrofuran is added slowly by syringe. The reaction mixture is stirred at −78° C. an additional 15 min and then quenched by addition of saturated aqueous ammonium chloride solution. Ethyl acetate (50 ml) is added and the organic phase is separated, washed with water (2×10 ml) and brine and dried over magnesium sulfate. Removal of solvents in vacuo gives a white solid which is chromatographed on a short silica gel column (40% ether in petroleum ether) to yield (3S,4R)-1-(t-butyldimethylsilyl)-3-[(R)-1-(t-butyldimethylsilyloxy)ethyl]-4-(3-benzyloxycarbonyl-2-hydroxypropyl)azetidin-2-one n.m.r. (CDCl$_3$) δ7.32(s,5), δ5,1(s,2), δ4.0(m,3), δ2,4–3,8(m,4),δ2.0(m,2), δ1.25(overlapping d,3), δ0.95(s,9), δ0.9(s,9), δ0.3(s,6), δ0.18(s,6).

EXAMPLE 11

Preparation of
(3S,4R)-1-(t-Butyldimethylsilyl)-3-[(R)-1-(t-butyldimethylsilyloxy)ethyl]-4-[3-(4-nitrobenzyl)oxycarbonyl-2-hydroxypropyl]azetidin-2-one

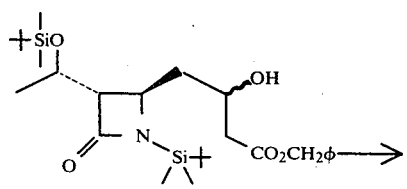

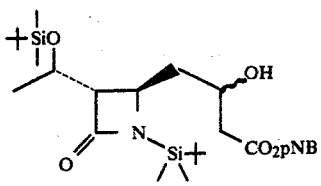

A mixture of (3S,4R)-1-(t-butyldimethylsilyl)-3-[(R)-1-(t-butyldimethylsilyloxy)ethyl]-4-(3-benzyloxycarbonyl-2-hydroxypropyl)azetidin-2-one (1.00 mmol), sodium bicarbonate (1.00 mmol) and 10% Pd/C in 20 ml of 4:1 tetrahydrofuran-H₂O is hydrogenated at 40 psi on a Parr shaker for 30 min. The mixture is then filtered through Celite and the catalyst is washed with 10 ml of water. The combined washings and filtrate are concentrated i.v. to 2 ml and lyophilized. The resulting fluffy white solid is dissolved in 5 ml of anhydrous dimethylformamide and p-nitrobenzyl bromide (216 mg, 1.00 mmol) is added in one portion. The resulting solution is stirred at room temperature for 3 hrs, then diluted with ether (50 ml) and washed with water (3×10 ml) and brine and dried over magnesium sulfate. The solvents are removed in vacuo and the residue is chromatographed on silica gel to yield (3S,4R)-1-(t-butyldimethylsilyl) 3[(R)-1-(t-butyldimethylsilyloxy)ethyl]-4-[3-(4-nitrobenzyl)oxycarbonyl-2-hydroxypropyl]azetidin-2-one, n.m.r. (CDCl₃) δ7.85(2d-aromatic,4), δ5,26(s,2), δ4.2(m,3), δ2,5–3.6(m,4) δ2.0(m,2), δ1.4(2 overlapping d,3), δ1.0(2s,18), δ0.25 (2s, 12).

EXAMPLE 12

Preparation of (3S,4R)-1-(t-Butyldimethylsilyl)-3-[(R)-1-(t-butyldimethylsilyloxy)ethyl]-4-[3-(4-nitrobenzyl)oxycarbonyl-2-oxopropyl]azetidin-2-one

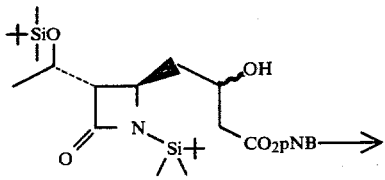

Anhydrous chromium trioxide (10.0 mmol) is added to a soution of anhydrous pyridine (20.0 mmol) in 30 ml of anhydrous methylene chloride. After stirring at room temperature for 15 min., the reaction mixture is treated all at once with a solution of (3S,4R)-1-(t-butyldimethylsilyl)-3-[(R)-1-(t-butyldimethylsilyloxy)ethyl]-4-[3-(4-nitrobenzyl)oxycarbonyl-2-hydroxypropyl]azetidin-2-one (1.00 mmol) in anhydrous methylene chloride (8 ml). The resulting mixture is stirred at room temperature for 5 min. The CH₂Cl₂ layer is decanted from the dark, tarry residue which is triturated with more CH₂Cl₂. The combined CH₂Cl₂ phase is concentrated in vacuo. The residue is triturated with ether (100 ml) and the ether extracts are filtered. The filtrate is washed with 5% aqueous sodium bicarbonate solution, 2.5 N HCl, 5% NaHCO₃ and brine, dried over magnesium sulfate and concentrated in vacuo to yield (3S,4R)-1-(t-butyldimethylsilyl)-3-[(R)-1-(t-butyldimethylsilyloxy)ethyl]-4-[3-(4-nitrobenzyl)oxycarbonyl-2-oxopropyl]azetidin-2-one. n.m.r. (CDCl₃) δ7.85(2d-aromatic, 4), δ5.27(s,2), δ4.05(m,2), δ3.6(s,2), δ2.4–3.2(dd overlapping ABq,3), δ1.2(d,3,J=6.6), δ0.9 (2s,18), δ0.22(s,6), δ0.05(s,6).

EXAMPLE 13

Preparation of (3S,4R)-3-[(R)1-hydroxyethyl]-4-[3-(4-nitrobenzyl)oxycarbonyl-2-oxopropyl]azetidin-2-one

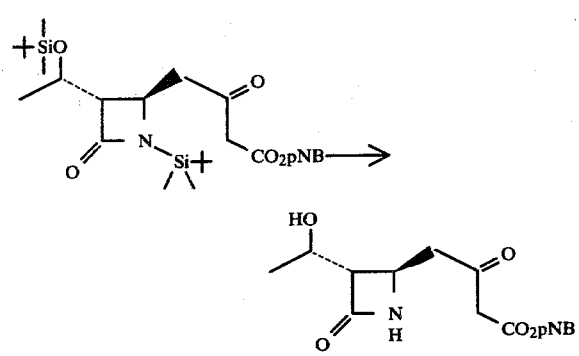

(3S,4R)-1-(t-butyldimethylsilyl)3-[(R)-1-(t-butyldimethylsilyloxy)ethyl]-4-[3-(4-nitrobenzyl)oxycarbonyl-2-oxopropyl]azetidin-2-one (7.9 mmol) is dissolved in 160 ml of 9:1 (v/v) methanol-water and cooled to 0° C. Concentrated hydrochloric acid (2.75 ml) is added and the resulting solution is stirred at 0° C. for 15 min., then allowed to warm to room temperature. The solution is stirred at room temperature for 2.5 hrs, then diluted with ethyl acetate (200 ml) and washed with water, saturated aqueous sodium bicarbonate solution and brine, dried over magnesium sulfate and concentrated in vacuo to yield (3S, 4R)-3-[(R)1-hydroxyethyl]-4-[3-(4-nitrobenzyl)oxycarbonyl-2-oxopropyl]-azetidin-2-one.

EXAMPLE 14

Preparation of (3S,4R)-3-[(R)-1-hydroxyethyl]-4-[3-(4-nitrobenzyl)oxycarbonyl-2-oxo-3-diazopropyl]azetidin-2-one

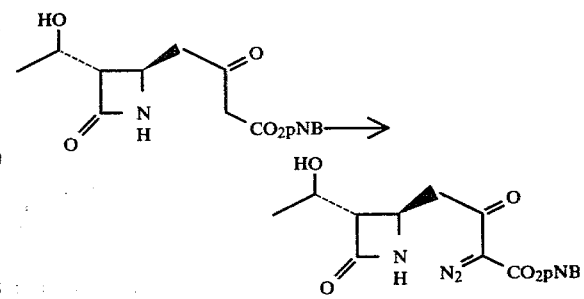

Triethylamine(263 mg, 2.6 mmol) is added by syringe to a mixture of (3S,4R)-3-[(R)-1-hydroxyethyl]-4-[3-(4- nitrobenzyl)oxycarbonyl-2-oxopropyl]azetidin-2-one(253 mg, 0.72 mmol) and p-carboxybenzene sulfonylazide (196 mg, 0.84 mmol) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 222 mg, (81% overall from (3S, 4R)-1-(t-butyldimethylsilyl)-3-[(R)-1-(t-butyl dimethylsilyloxy)ethyl]-4-[3-(4-nitrobenzyl)oxycarbonyl-2-oxopropyl]azetidin-2-one) of (3S,4R)-3-(R)-1-hydroxyethyl)-4-[3-(4-nitrobenzyl)oxycarbonyl-2-oxo-3-diazopropyl]azetidin-2-one as a white solid m.p. (dec.) 163° C. IR(CHCl₃, CM⁻¹) 3410, 2132, 1756, 1718, 1650, 1350, 1280, 1120; n.m.r. (CDCl₃) δ7.9(2d-aromatic,4), δ5.4(s,2), δ6.2(brs,1), δ4.1(m,2), δ2.6–3.6(m,4), δ1.32(d,3,J=6.2).

EXAMPLE 15

Preparation of (5R,6S)p-Nitrobenzyl 6-[(R)1-hydroxyethyl]-1-azabicyclo[3.2.0]heptan-3,7-dione-2-carboxylate

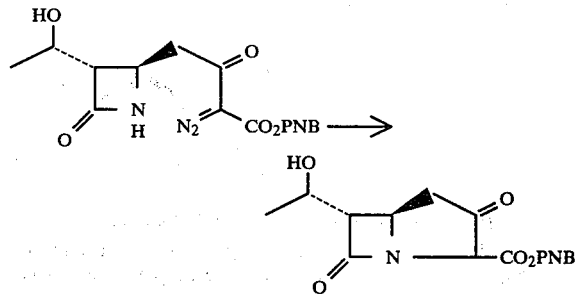

A suspension of (3S,4R)-3-[(R)-1-hydroxyethyl]-4-[3-(4-nitrobenzyl)oxycarbonyl-2-oxo-3-diazopropyl]azetidin-2-one (56.4 mg, 0.15 mmol) and rhodium (II) acetate (0.1 mg) in dry benzene (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield (5R, 6S) p-nitrobenzyl 6-[(R)-1-hydroxyethyl]-1-azabicyclo[3.2.0]heptan-3,7-dione-2-carboxylate, 51 mg. (98%) as a colorless oil which slowly crystallized at room temperature (22° C.).

Physical Properties:

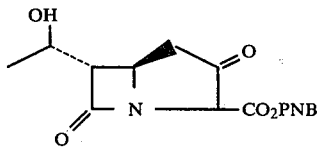

PNB = p-nitrobenzyl n.m.r.: (300 MHz, CDCl₃) δ8.26, 7.54 (aromatic, 4), 5.29 (AB,2), 4.77 (s,1), 4.32(dg,I,J=6.6,7), 4.16(ddd,1,J=7,7.5,2.2), 3.21(dd,1,J=7,2.2), 2.94(dd,1,J=19.5,7) 2.50(dd,1,J=19.5,7.5), 2.2(brs,1), 1.37(d,3,J=6.6).

I.R.: (CHCl₃, CM⁻¹) 1770, 1758, 1610, 1522, 1353. m.p. 110°–111° C.

EXAMPLE 16

Preparation of p-Nitrobenzyloxycarbonylaminoethanethiol

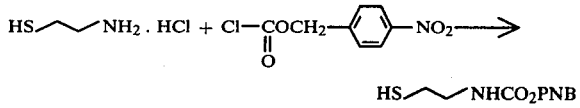

To 600 diethyl ether (Et₂O) –75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl₃): 8.18 (d, J=8 Hz, aromatic protons ortho to nitro), 7.47 (d, J=8 Hz, aromatic protons meta to nitro), 5.27 (—NH—), 5.20 (s, CH₂-NH—), 2.67 (m, —CH₂—SH), 1.35 (t, J=8.5 Hz, —SH) in ppm downfield from TMS. IR (CHCl₃ solution): carbonyl- 1725 cm⁻¹. M.S.: molecular ion-256, (M-47) at 209, (M-136) at 120, +CH₂φpNO₂ at 136.

EXAMPLE 15

Preparation of (5R,6S) p-Nitrobenzyl 3-[2-(p-nitrobenzyloxycarbonyl)aminoethylthio]-6-[(R)-1-hydroxyethyl]-1-azabicyclo[3.2.0]hept-2-en-7-one-2-carboxylate

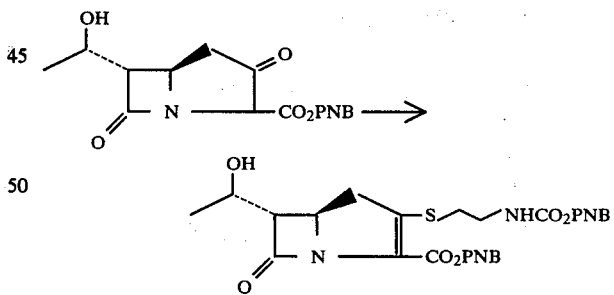

(5R,5S) p-Nitrobenzyl 6-[(R)1-hydroxyethyl]-1-azabicyclo[3.2.0]heptan-3,7-dione-2-carboxylate (51 mg, 0.147 mmol) is dissolved in acetonitrile (3 ml) and the resulting solution is cooled to 0° C. Diisopropylethylamine (22 mg, 0.17 mmol) is added by syringe and the resulting solution is stirred at 0° C. for 1 minute prior to the addition of a solution of freshly recrystallized p-toluene sulfonic anhydride (51 mg, 0.156 mmol) in dry acetonitrile (1 ml). The resulting solution is stirred at 0° C. for 1 hour to provide (5R, 6S)p-nitrobenzyl 3-(p-toluenesulfonyloxy)-6-[(R)-1-hydroxyethyl]-1-azabicyclo[3.2.0]hept-2-en-7-one-2-carboxylate, then cooled to −25° C. Diisopropylethylamine (80.5 mg, 0.624 mmol) is added by syringe followed shortly thereafter by a solution of N-p-nitrobenzyloxycarbonylcysteamine (40 mg, 0.156 mmol) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield a yellow oil which is chromatographed on a silica gel plate (ethyl acetate, $R_f=0.4$) to yield (5R,6S) p-nitrobenzyl-3-[2-(p-nitrobenzyloxycarbonyl)aminoethylthio]-6-[(R)-1-hydroxyethyl]-1-azabicyclo[3.2.0]-hept-2-en-7-dione-2-carboxylate as a yellow solid, m.p. 167°–169° C. IR(-Nujol mull) 1773 and 1690 cm$^{-1}$; n.m.r. (CDCl$_3$)$\delta$7.54–8.26 (overlapping ABq,4), $\delta$5.40(ABq,2), $\delta$5.22(s,2), $\delta$4.27(m,2), $\delta$3.47(m), $\delta$3.23(dd, 1), $\delta$3.14(dd, 1) $\delta$3.40(dd,1), $\delta$3.04(m,2), $\delta$1.37(d, 3).

EXAMPLE 18

Preparation of Thienamycin

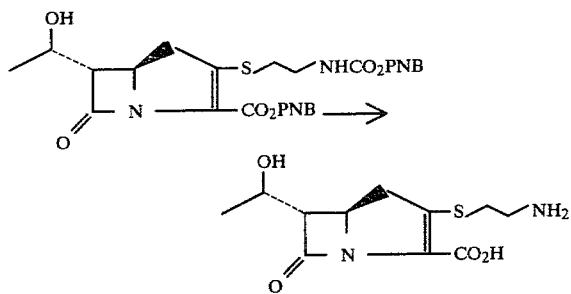

A mixture of N-p-nitrobenzyloxycarbonyl thienamycin p-nitrobenzyl ester (10 mg, 0.017 mmol) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water (3×3 ml). The combined filtrate and washings are extracted with ethyl acetate-ethyl ether then concentrated to ~3 ml and lyophilized. The resulting white powder is identical to natural thienamycin in all respects.

EXAMPLE 19

Preparation of Benzyl (4-S)-azetidin-2-one-4-carboxylate

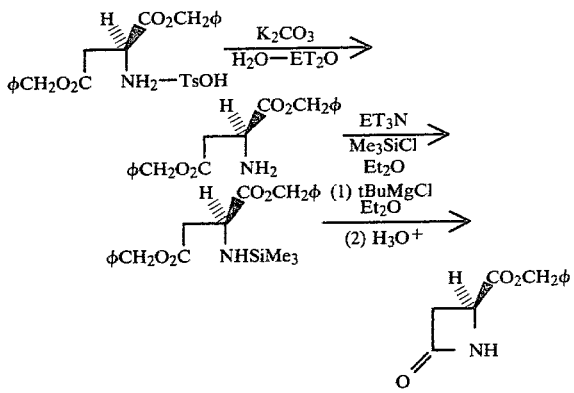

A mixture of dibenzyl (S)-asparate p-toluenesulfonic acid salt (48.6 g, 0.1 mole), diethylether (300 ml), water (100 ml), and saturated aqueous potassium carbonate (50 ml) is shaken vigorously. The layers are separated and the aqueous portion is extracted with more ether (2×100 ml). The combined ethereal extracts are washed with brine, dried with magnesium sulfate, filtered, and evaporated under vacuum to afford dibenzyl (S)-aspartate (31.5 g) as a water white liquid.

The dibenzyl (S)-aspartate in anhydrous diethyl ether (200 ml) is cooled in an ice bath and stirred under a nitrogen atmosphere while trimethylchlorosilane (12.7 ml, 0.1 mole) and triethylamine (14.0 ml, 0.1 mole) are added successively over a few minutes. The cooling bath is removed and the mixture is stirred at room temperature for 2 hours. The mixture is then filtered under a blanket of nitrogen into a three-neck, one-liter, round bottom flask fitted with a sintered glass funnel, vacuum-nitrogen inlet, and a mechanical stirrer. Additional anhydrous ether (2×50 ml) is used to wash the precipitate of tri-.

EXAMPLE 20

Following the procedure of the foregoing Examples and text, the azetidinones of Table I are obtained. Table I is annotated under the 'Remarks' column where appropriate.

TABLE I

| Compound | R$^6$ | R$^7$ | Remarks |
|---|---|---|---|
| 1. | (CH$_3$)$_2$CH | H | As in Example 4, but substitute equivalent amount of isopropyl iodide for acetaldehyde. |
| 2. | CH$_3$ | H | As in Example 4, but using an equivalent amount of methyl iodide for acetaldehyde. |
| 3. | HOCH$_2$ | CH$_3$ | As in Example 4, but use compound 2., and excess formaldehyde |

TABLE I-continued

[Structure: β-lactam with R6, R7 substituents on the ring carbons, N-Si(t-Bu)(CH3)2 on nitrogen, and -C(SCH3)3 side chain]

| Compound | R⁶ | R⁷ | Remarks |
|---|---|---|---|
| | | | introduced as a gas just above surface of stirred solution. |
| 4. | φCH₂CH(OH)— | H<br>φ = phenyl | As in Example 4, but using an equivalent amount of phenyl acetaldehyde for acetaldehyde. |
| 5. | CH₃CH(OH)— | CH₃ | Using the procedure of Example 4 upon compound 2 of Table I. |
| 6. | φCH₂ | H | As in Example 4, but substitute benzylbromide for acetaldehyde. |
| 7. | CH₃CH(OH)— | φCH₂ | As in Example 4, but using compound 6 as substrate. |
| 8. | CH₃CH(OMs)—<br>Ms = mesyl | H | Obtained from the product of Example 4 and methanesulfonyl chloride and triethylamine in methylene chloride at 0°. |
| 9. | CH₃CH(N₃)— | H | Obtained from compound 8 on treatment with LiN₃ in DMF at 60°. |
| 10. | CH₃CH(NH₂)— | H | Obtained from compound 9 by reduction with H₂S and Et₃N in CH₂Cl₂. |
| 10a. | CH₃CH(NHCO₂PNB)— | H | Obtained from compound 9 on treatment with ClCO₂PNB and DMPA in CH₂Cl₂ at 0°. |
| 11. | (CH₃)₂CHCH(OH)— | H | As in Example 4, but substituting isobutyraldehyde for acetaldehyde. |
| 12. | (CH₃)₂CHCH₂CH₂CH(OH)— | H | As in Example 4, but substitute 5-methyl valeraldehyde for acetaldehyde |
| 13. | cyclopropyl-CH(OH)— | H | As in Example 4, but substitute cyclopropane carboxaldehyde for acetaldehyde. |
| 14. | CF₃CH(OH)— | H | As in Example 4, but substitute trifluoroacetaldehyde for acetaldehyde. |
| 15. | tBuMe₂SiOCH₂CH(OH)— | H | As in Example 4, but substitute t-butyldimethylsilyloxyacetaldehyde for acetaldehyde. |
| 16. | HOCH₂CH₂ | H | As in Example 4, but substitute oxirane for acetaldehyde. |
| 17. | CH₃CH₂CH₂CH(OH)— | H | As in Example 4, but substitute butyraldehyde for acetaldehyde. |
| 18. | CH₃CH₂CH(OH)— | H | As in Example 4, but substitute propionaldehyde for acetaldehyde. |
| 19. | FCH₂CH(OH)— | H | As in Example 4, but substitute fluoroacetaldehyde for acetaldehyde. |
| 20. | cyclopropyl-CH₂CH(OH)— | H | As in Example 4, but substitute cyclopropylacetaldehyde for acetaldehyde. |
| 21. | CH₃CH₂ | H | As in Example 4, but |

TABLE I-continued $$R^6-\overset{R^7}{\underset{O}{\underset{\|}{C}}}\overset{}{\underset{N}{\triangle}}\overset{SCH_3}{\underset{SCH_3}{\overset{|}{C}-SCH_3}}$$

$$\underset{N}{\underset{\underset{Si}{|}}{\bigtriangleup}}$$

| Compound | R⁶ | R⁷ | Remarks |
|---|---|---|---|
| | | | substitute ethyliodide for acetaldehyde. |
| 22. | CH₃ | CH₃ | As in Example 4, but use compound 2 and substitute methyliodide for acetaldehyde. |
| 23. | ▷—CH₂ | H | As in Example 4, but substitute cyclopropyl-methylbromide for acetaldehyde. |
| 24. | HOCH₂CH₂ | CH₃ | As in Example 4, but use compound 2 and substitute oxirane for acetaldehyde. |
| 25. | OH-cyclopentyl | H | As in Example 4, but use cyclopentanone instead of acetaldehyde. |
| 25a. | ClCH₂—CH(OH)— | H | As in Example 5, Step A, but use an equivalent amount of chloroacetylimidazole instead of acetylimidazole. |
| 25b. | ClCH₂—CH(OH)— | CH₃ | As in Example 20, Table I, No. 25a, but starting with azetidinone of Example 20, Table I, No. 3. |
| 26. | CF₃C(O)— | H | As in Example 5, Step A, but use ethyl trifluorothiolacetate instead of N-acetylimidazole. |
| 27. | CF₃CH(OH)— | H | As in Example 6, but substitute product No. 26, Table I, Example 20, and use sodium borohydride as reductant. |
| 28. | N₃CH₂CH(OH)— | H | As in Example 4, but use azidoacetaldehyde instead of acetaldehyde. |
| 29. | PNBOCCH₂(O)— | H | As in Example 4 but substituted p-nitrobenzyl bromoacetate for acetaldehyde. |
| 30. | MeOCH₂C(O)— | H | As in Example 5, Step A, but substituted N-methoxyacetyl imidazole for N-acetyl imidazole. |
| 31. | MeOCH₂CH(OH)— | H | Obtained by employing the procedure of Example 6 on compound No. 30, Table I, Example 14. |
| 32. | CF₂CHCH(O)— | H | As in Example 5, Step A, but substitute ethyl difluorothiolacetate for N-acetylimidazole. |
| 33. | CF₂CHCH(OH)— | H | Obtained from No. 32, above, using the procedure of Example 6, but substituting sodium borohydride as the reducing agent. |
| 34. | PNBOCOCH₂(O)— | CH₃ | Obtained from No. 3, Table I, Example 20 with p-nitrobenzyl chloroformate and 4-dimethylaminepyridine in methylene chloride. |

TABLE I-continued

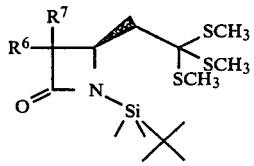

| Compound | R⁶ | R⁷ | Remarks |
|---|---|---|---|
| 35. | PNBOCOCH₂CH₂ (C=O) | H | Obtained from No. 16 Table I, Example 20, by reaction with p-nitrobenzyl chloroformate and triethylamine in methylene chloride. |
| 36. | PNBOCOCH₂CH₂ (C=O) | CH₃ | Obtained from No. 24 Table I, Example 20 as described for the preceeding compound. No. 35. |
| 37. | HOCH₂ | H | As in Example 4, but use excess formaldehyde instead of acetaldehyde. |
| 38. | PNBOCOCH₂ (C=O) | H | Obtained from compound 36, above, and p-nitrobenzyl-chloroformate in methylene chloride containing 4-dimethylaminopyridine. |
| 39. | CH₂=CHCH(OH) | H | As in Example 4, but use equivalent amount of CH₂=CHCHO instead of acetaldehyde. |

EXAMPLE 21

Following the foregoing Examples and text, particularly Example 15, the representative intermediates of the present invention are obtained when the indicated substitution from, inter alia, Example 20 is made into the scheme of Example 15.

TABLE II

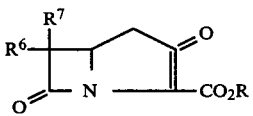

| Compound | R⁶ | R⁷ | Remarks |
|---|---|---|---|
| (1.) | (CH₃)₂CH | H | |
| (2.) | CH₃ | H | |
| (3.) | PNBOCOCH₂ (C=O) | CH₃ | The primary alcohol, No. 3 Table I, Example 20 is protected as shown by reacting with an equivalent amount of ClCO₂PNB in the presence of DMAP (dimethylaminopropane in methylene chloride. |
| (4.) | φCH₂CH(OH) | H | |
| (5.) | CH₃CH(OH) | CH₃ | |
| (6.) | φCH₂ | H | |
| (7.) | CH₃CH(OH) | φCH₂ | |
| (8.) | CH₃CH(N₃) | H | |
| (9.) | CH₃CH(NHCO₂PNB) | H | |
| (10.) | (CH₃)₂CHCH(OH) | H | |
| (11.) | (CH₃)₂CHCH₂CH₂CH(OH) | H | |
| (12.) | ▷—CH(OH) | H | |
| (13.) | CF₃CH(OH) | H | |
| (14.) | HOCH₂—CH(OH)— | H | |
| (15.) | PNBOCOCH₂CH₂ (C=O) | H | Protected as described for No. 3, Table II, Example 21. |
| (16.) | CH₃CH₂CH₂CH(OH) | H | |
| (17.) | CH₃CH₂CH(OH) | H | |
| (18.) | FCH₂CH(OH) | H | |
| (19.) | ▷—CH₂CH(OH) | H | |
| (20.) | CH₃CH₂ | H | |
| (21.) | CH₃ | CH₃ | |
| (22.) | ▷—CH₂ | H | |

TABLE II-continued

| Compound | R⁶ | R⁷ | Remarks |
|---|---|---|---|
| (23.) | PNBOCOCH₂CH₂ (O=C) | CH₃ | Protected as described for No. 3, Table II, Example 21. |
| (24.) | cyclopentyl-OH | H | |
| (25.) | N₃CH₂CH(OH) | H | |
| (25a.) | ClCH₂CH(OH)— | H | |
| (25b.) | ClCH₂CH(OH)— | CH₃ | |
| (26.) | PNBOCCH₂ (O=C) | H | |
| (27.) | MeOCH₂CH(OH) | H | |
| (28.) | CF₂CHCH(OH) | H | |
| (29.) | PNBOCOCH₂ (O=C) | H | |

TABLE II-continued

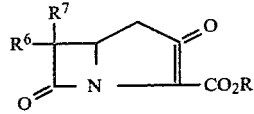

| Compound | R⁶ | R⁷ | Remarks |
|---|---|---|---|
| (30.) | CH₂=CHCH(O—) | H | |

R = PNB (p-nitrobenzyl)
φ = phenyl

EXAMPLE 22

Following the foregoing Examples and text, the following compounds are prepared in representative demonstration of the disclosed process. In the following Table, the resulting compounds are taken from starting materials which are made available by the foregoing text and examples—particularly Table II of Example 21. The column labelled "Remarks and Reagents" annotates the established procedure where necessary to obtain the indicated compound. In most instances the compounds are deblocked according to the procedure described in Example 12. However, when the SR⁸ side chain does not contain a basic function, the final product I is more conveniently isolated as the sodium salt (M=Na); which result is facilitated by conducting the deblocking in a slight excess of NaHCO₃. In any event, when either R⁶ or R⁷ bears a basic group, the final product I is most conveniently isolated as the free acid (M=H), rather than the sodium salt. It should be noted that compounds designated as "free acids" in reality are isolated as inner salts as a consequence of their zwitterionic nature.

TABLE III

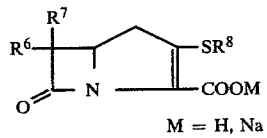

M = H, Na

| Compound | R⁶ | R⁷ | R⁸ | Remarks, Reagents |
|---|---|---|---|---|
| (1.) | (CH₃)₂CH | H | φ | As in Example 11, but substitute HSφ for HSCH₂CH₂NHCO₂PNB. Deblock as described in Example 12 and isolate product as Na salt. M = Na. |
| (2.) | CH₃ | H | CH₂φ | HSCH₂φ; M = Na |
| (3.) | HOCH₂ | CH₃ | CH₂CH₂CH₂NH₂ | HSCH₂CH₂CH₂NHCO₂PNB; M = H. |
| (4.) | φCH₂CH(OH—) | H<br>φ = phenyl | CH₂C(CH₃)₂NH₂ | HSCH₂C(CH₃)₂NHCO₂PNB; M = H. |
| (5.) | CH₃CH(OH) | CH₃ | CH₂CH₂NH₂ | M = H |
| (6.) | CH₃CH(OH) | CH₃CH(OH) | CH₂CH₂NH₂ | M = H |
| (7.) | CH₃CH(OH) | φCH₂ | CH₂CH₂N(CH₃)₂ | HSCH₂CH₂N(CH₃)₂; M = H |
| (8.) | CH₃CH(NH₂) | H | CH₂CH₂NH₂ | M = H |
| (9.) | (CH₃)₂CHCH(OH) | H | CH₂-(imidazolyl) | HSCH₂-(imidazolyl); M = Na |

| | | | | |
|---|---|---|---|---|
| (10.) | (CH₃)₂CHCH₂CH₂CH(OH) | H | 3-methylpyridine | 3-HS-pyridine; M = H |
| (11.) | cyclopropyl-CH(OH) | H | 2-(CH₂)-pyridine | 2-(HSCH₂)-pyridine; M = H |
| (12.) | CF₃CH(OH) | H | CH₂CH₂NH₂ | M = H |
| (13.) | HOCH₂CH(OH) | H | CH₂CH₂NH₂ | M = H |
| (14.) | HOCH₂CH₂ | H | CH₂CH₂—N(piperazine)NCH₃ | HSCH₂CH₂—N(piperazine)NCH₃; M = H |
| (15.) | CH₃CH₂CH₂CH(OH) | H | 2-(CH₂)-pyridine | 2-(HSCH₂)-pyridine; M = H |
| (16.) | CH₃CH₂CH(OH) | H | 2-(CH₂NH₂)-phenyl | 2-(CH₂NHCO₂PNB)-phenyl-HS; M = H |
| (17.) | FCH₂CH(OH) | H | CH₂CH₂NH₂ | |
| (18.) | cyclopropyl-CH₂CH(OH) | H | CH₂CH₂CO₂H | HSCH₂CH₂CO₂PNB; Product isolated as disodium salt. |
| (19.) | CH₃CH₂ | H | CH₂CH₂NH₂ | |
| (20.) | CH₃ | CH₃ | 1-methyl-tetrazol-5-yl | HS-(1-methyl-tetrazol-5-yl); M = Na |
| (21.) | cyclopropyl-CH₂ | H | CH₂CH₂OH | HSCH₂CH₂OH; M = Na |
| (22.) | HOCH₂CH₂ | CH₃ | CH₂CH₂CH₂CH₂NH₂ | HSCH₂CH₂CH₂CH₂NHO₂PNB; M = H |
| (23.) | cyclopentyl-OH | H | CH₂C(CH₃)₂CH₂NH₂ | CH₂C(CH₃)₂CH₂NHCO₂PNB; M = H |
| (24.) | 3-OH-cyclopentyl | H | CH₂CH₂NH₂ | M = Na |
| (25.) | 2-methyl-cyclopentyl-OH | H | CH₂CH₂NH₂ | M = Na |
| (26.) | CH₃CH(OH) | H | S-CH₂CH₂CH₃ | HS-CH₂CH₂CH₃; M = Na |
| (27.) | CH₃CH(OH) | H | S-CH₂CH₂OH | HS-CH₂CH₂OH; M = Na |
| (28.) | CH₃CH(OH) | H | S-CH₂CH₂NH₂ | HS-CH₂CH₂NHCO₂PNB; M = H |
| (29.) | CH₃CH(OH) | H | S-CH₂CH₂NHC(O)CH₃ | HS-CH₂CH₂NHC(O)CH₃; M = Na |

TABLE III-continued

| | | | | |
|---|---|---|---|---|
| (30.) | CH₃CH(OH)— | H | S—CH₂—CH(NH₂)— | HS—CH₂—CH(NHCO₂PNB)—; M = H |
| (31.) | CH₃CH(OH)— | H | S—CH₂—CH₂—NH₂ | HS—CH₂—CH₂—NHCO₂PNB; M = H |
| (32.) | CH₃CH(OH)— | H | S—CH(CH₃)—CH₂—NH₂ | HS—CH(CH₃)—CH₂—NHCO₂PNB; M = H |
| (33.) | CH₃CH(OH)— | H | S—C(CH₃)₂—NH₂ | HS—C(CH₃)₂—NHCO₂PNB; M = H |
| (34.) | CH₃CH(OH)— | H | S—CH₂—CH(CH₃)—NH₂ | HS—CH₂—CH(CH₃)—NHCO₂PNB; N = H |
| (35.) | CH₃CH(OH)— | H | S—CH₂—CH₂—N(pyrrolidine) | HS—CH₂—CH₂—N(pyrrolidine); M = H |
| (36.) | CH₃CH(OH)— | H | S—CH₂—CH₂—N(CH₃)₂ | HS—CH₂—CH₂—N(CH₃)₂; M = H |
| (37.) | CH₃CH(OH)— | H | S—CH₂—CH(OH)—CH₂—NH₂ | HS—CH₂—CH(OH)—CH₂—NHCO₂PNB; M = H |
| (38.) | CH₃CH(OH)— | H | S—CH₂—CH(COOH)—NH₂ | HS—CH₂—CH(CO₂PNB)—NHCO₂PNB; M = H |
| (39.) | CH₃CH(OH)— | H | S—CH₂—CH₂—C(=NH)NH₂ | HS—CH₂—CH₂—C(=NH)NHCO₂PNB; M = H |
| (40.) | CH₃CH(OH)— | H | S—CH₂—CH(NH₂)—CH₂OH | HS—CH₂—CH(NHCO₂PNB)—CH₂OH; M = H |
| (41.) | CH₃CH(OH)— | H | S—CH₂—CH₂—NHφ | M = H |
| (42.) | CH₃CH(OH)— | H | S—CH₂—CH₂—N(H)C(CH₃)₃ | HS—CH₂—CH₂—N⁺(CO₂PNB)—  M = H |
| (43.) | CH₃CH(OH)— | H | Sφ | M = Na |
| (44.) | CH₃CH(OH)— | H | S—(o-NH₂—C₆H₄) | HS—(o-NHCO₂PNB—C₆H₄); M = H |
| (45.) | CH₃CH(OH)— | H | S—(3-pyridyl) | HS—(3-pyridyl); M = H |
| (46.) | CH₃CH(OH)— | H | S—(1-methyl-1H-tetrazol-5-yl) | M = Na |
| (47.) | CH₃CH(OH)— | H | S—CH₂—C₆H₅ | M = Na |
| (48.) | CH₃CH(OH)— | H | S—CH₂—(2-pyridyl) | M = H |
| (49.) | CH₃CH(OH)— | H | S—CH₂—(3-pyridyl) | M = H |
| (50.) | CH₃CH(OH)— | H | S—(2-amino-thiazol-4-yl) | HS—(2-NHCO₂PNB-thiazol-4-yl); M = H |

TABLE III-continued

| | | | | |
|---|---|---|---|---|
| (51.) | OH<br>\|<br>CH₃CH | H | [imidazoline ring with S-CH₂ substituent] | M = Na |
| (52.) | OH<br>\|<br>CH₃CH | H | [thiazole ring: S-CH=C(S-)-N=C-NH₂] | HS-CH=C(-S-)-N=C-NHCO₂PNB<br>M = H |
| (53.) | OH<br>\|<br>CH₃CH | H | S-CH₂CH₂-N(piperazine)NCH₃ | M = H |
| (54.) | OH<br>\|<br>CH₃CH | H | S-(piperidine)-NCH₃ | M = H |
| (55.) | OH<br>\|<br>CH₃CH | H | [imidazoline: S-CH₂-CH(N=CH-CH=N-H)] | [HS-CH₂-CH(N=CH-CH=N-CO₂PNB)] ; M = H |
| (56.) | OH<br>\|<br>CH₃CH | H | S-CH₂CH₂-O-CH₂CH₂-NH₂ | HS-CH₂CH₂-O-CH₂CH₂-NHCO₂PNB<br>M = H |
| (57.) | OH<br>\|<br>CH₃CH | H | S-CH₂CH₂-N(CH₃)-CH₂CH₂-NH₂ | HS-CH₂CH₂-N(CH₃)-CH₂CH₂-NHCO₂PNB;<br>M = H |

| Compounds | | |
|---|---|---|
| 58–89 | Compounds 58–89 correspond sequentially to compounds 26–57, above, except that the value for R⁶ is taken as CH₃CH₂ rather than the CH₃C(OH)H of Compounds 26–57. | |
| 90–121 | Compounds 90–121 correspond sequentially to compounds 26–57, above, except that the value for R⁶ is taken as rather than the CH₃C(OH)H of Compounds 26–57. | OH<br>\|<br>Cl₂CHCH |
| 122–153 | Compounds 122–153 correspond sequentially to compounds 26–57, above, except that the value for R⁶ is taken as rather than the CH₃C(OH)H of Compounds 26–57. | OH<br>\|<br>CF₃CH |
| 154–185 | Compounds 154–185 correspond sequentially to compounds 26–57, above, except that the value for R⁶ is taken as rather than the CH₃C(OH)H of Compounds 26–57. | OH<br>\|<br>HOCH₂CH |
| 186–217 | Compounds 186–217 correspond sequentially to compounds 26–57, above, except that the value for R⁶ is taken as rather than the CH₃C(OH)H of Compounds 26–57. | OH<br>\|<br>ClCH₂CH |
| 218–249 | Compounds 218–249 correspond sequentially to compounds 26–57, above, except that the value for R⁶ is taken as rather than the CH₃C(OH)H of Compounds 26–57. | OH<br>\|<br>CH₃CH₂CH |
| 250–281 | Compounds 250–281 correspond sequentially to compounds 26–57, above, except that the value for R⁶ is taken as rather than the CH₃C(OH)H of Compounds 26–57. | OH<br>\|<br>▷—CH |
| 282–313 | Compounds 282–313 correspond sequentially to compounds 26–57, above, except that the value for R⁶ is taken as rather than the CH₃C(OH)H of Compounds 26–57. | OH<br>\|<br>H₂NCH₂CH |
| 314–345 | Compounds 314–345 correspond sequentially to compounds 26–57, above, except that the value of R⁶ is taken as rather than the CH₃C(OH)H of Compounds 26–57. | OH<br>\|<br>CF₂HC— |
| 346–377 | Compounds 346–377 correspond sequentially to compounds 26–57, above, except that the value for R⁶ is taken as HOCH₂ rather than the CH₃C(OH)H of Compounds 26–57. | |
| 378–409 | Compounds 378–409 correspond sequentially to compounds 26–57, above, except that the value for R⁶ is taken as HO₂CCH₂ rather than the CH₃C(OH)H of Compounds 26–57. | |
| 410–441 | Compounds 410–441 correspond sequentially to compounds 26–57, above, except that the value for R⁶ is taken as rather than the CH₃C(OH)H of Compounds 26–57. | OH<br>\|<br>CH₃OCH₂CH |
| 442–473 | Compounds 442–473 correspond sequentially to compounds 26–57, above, except that the value for R⁶ is taken as rather than the CH₃C(OH)H of Compounds 26–57. | OH<br>\|<br>(CH₃)₃CCH₂CH |

What is claimed is:

1. A compound having the structural formula:

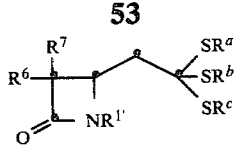

wherein R[1'] is hydrogen or a readily removable trialkylsilyl protecting group; R[a], R[b] and R[c] are independently selected from the group consisting of alkyl having 1-6 carbon atoms, phenyl and phenylalkyl having 7-10 carbon atoms; and wherein R[6] and R[7] are independently selected from the group consisting of: hydrogen; mono substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; phenyl; aralkyl, aralkenyl, and aralkynyl wherein the aryl moiety is phenyl and the aliphatic portion has 1-6 carbon atoms; wherein the substituent or substituents relative to the above-named radicals are selected from the group consisting of: chloro, bromo, fluoro, R[1],

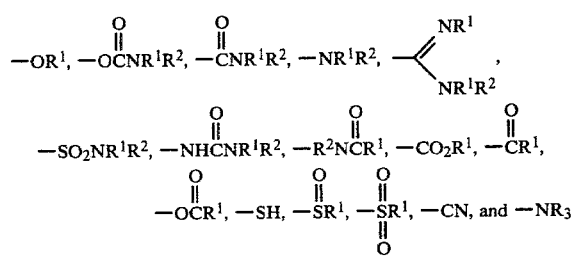

wherein, relative to the above listed substituents on R[6], and R[7], the group R[1] and R[2] are independently selected from: hydrogen, alkyl, alkenyl and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; R[6] and R[7] are not both hydrogen at the same time; when R[6]/R[7] is hydrogen, then R[7]/R[6] is not

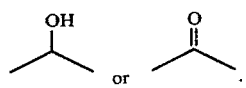

2. A compound according to claim 1, wherein R[a], R[b] and R[c] are methyl.

3. A compound according to claim 1 wherein R[7] is hydrogen and R[6] is selected from the group consisting of:

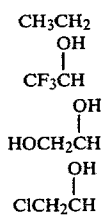

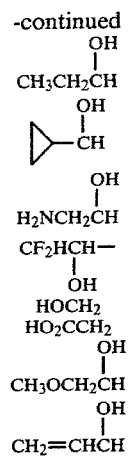

4. A compound according to claim 1 wherein R[6] and R[7] are independently selected from the group consisting of: hydrogen; monosubstituted and unsubstituted: alkyl, alkenyl and alkynyl having from 1-10 carbon atoms, cycloalkyl, cycloalkyalkyl and alkylcycloalkyl, having 3-6 carbon atoms in the cycloalkyl ring and 1-6 carbon atoms in the alkyl moieties; phenyl; aralkyl, aralkenyl, and aralkynyl wherein the aryl moiety is phenyl and the aliphatic portion has 1-6 carbon atoms; wherein the substituent or substituents relative to the above-named radicals are selected from the group consisting of:

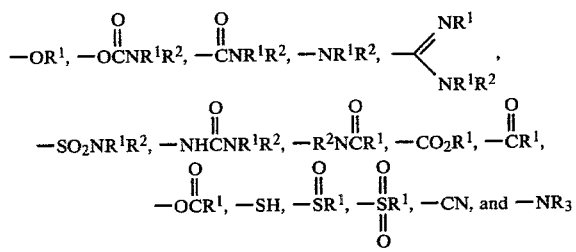

wherein, relative to the above listed substituents on R[6], and R[7], the groups R[1] and R[2] are independently selected from: hydrogen, alkyl, alkenyl and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties, phenyl; aralkyl, aralkenyl, and aralkynyl wherein the aryl moiety is phenyl and the aliphatic portion has 1-6 carbon atoms.

5. A compound according to claim 1 wherein R[7] is hydrogen or methyl.

6. A compound according to claim 5 wherein R[6] is selected from the group consisting of: substituted and unsubstituted: alkyl, alkenyl and cycloalkylalkyl wherein the substituent or substituents are selected from hydroxyl, alkoxyl having from 1-6 carbon atoms, phenoxy, amino, and carboxy.

7. A compound according to claims 5 or 6 wherein R[6] is selected from the group consisting of alkyl, cycloalkylalkyl, alkyl substituted by one or more hydroxyl groups, or cycloalkylalkyl substituted by one or more hydroxyl groups.

8. A compound according to claim 5 wherein R[7] is hydrogen.

* * * * *